(12) United States Patent
Cohen

(10) Patent No.: US 8,778,416 B2
(45) Date of Patent: Jul. 15, 2014

(54) PHARMACEUTICAL COMPOSITIONS AND METHODS FOR THE TREATMENT AND PREVENTION OF CANCER

(75) Inventor: Shahar Cohen, Kiryat Bialik (IL)

(73) Assignee: Nayacure Therapeutics Ltd., Haifa (IL)

(*) Notice: Subject to any disclaimer, the term of this patent is extended or adjusted under 35 U.S.C. 154(b) by 0 days.

(21) Appl. No.: 13/578,402

(22) PCT Filed: Feb. 10, 2011

(86) PCT No.: PCT/IL2011/000146
§ 371 (c)(1),
(2), (4) Date: Nov. 5, 2012

(87) PCT Pub. No.: WO2011/099007
PCT Pub. Date: Aug. 18, 2011

(65) Prior Publication Data
US 2013/0052272 A1    Feb. 28, 2013

Related U.S. Application Data

(60) Provisional application No. 61/303,078, filed on Feb. 10, 2010.

(51) Int. Cl.
*A01N 65/00*    (2009.01)
(52) U.S. Cl.
USPC .......................................... 424/725
(58) Field of Classification Search
None
See application file for complete search history.

(56) References Cited

U.S. PATENT DOCUMENTS

2009/0291067 A1    11/2009    Park

FOREIGN PATENT DOCUMENTS

| WO | 2006019357 A1 | 2/2006 |
|---|---|---|
| WO | 2008014426 A2 | 1/2008 |
| WO | 2008020329 A2 | 2/2008 |
| WO | 2008087442 A1 | 7/2008 |
| WO | 2009098686 A2 | 8/2009 |
| WO | 2009098698 A2 | 8/2009 |

OTHER PUBLICATIONS

Szyf, M. "Therapeutic implications of DNA methylation" Future Oncol 1, 125-135 (2005).
Collas, P., et al. "Novel approaches to epigenetic reprogramming of somatic cells" Cloning Stem Cells 9, 26-32 (2007).
Hendrix, M.J. et al., "Reprogramming metastatic tumour cells with embryonic microenvironments" Nat Rev Cancer 7, 246-255 (2007).
Ingber D.E., "Can cancer be reversed by engineering the tumor microenvironment?" Semin Cancer Biol. 18(5):356-64 (2008).
Allegrucci C. et al., "Epigenetic reprogramming of breast cancer cells with oocyte extracts" Mol Cancer Jan. 13, 2011;10(1):7 doi: 10.1186/1476-4598-10-7 (2011).
Postovit et al., "Human embryonic stem cell microenvironment suppresses the tumorigenic phenotype of aggressive cancer cells" PNAS, 105(11):4329-4334 (2008).
International Search Report for PCT/IL2011/000146, issued Apr. 28, 2011.

*Primary Examiner* — Michael Meller
(74) *Attorney, Agent, or Firm* — Browdy and Neimark, PLLC

(57) ABSTRACT

The present invention concerns pharmaceutical compositions and methods for treating proliferative diseases, e.g. cancer using intracellular and extracellular extracts. These cell extracts can direct epigenetic reprogramming of the cancer cells and thereby reverse their neoplastic phenotype.

14 Claims, No Drawings

PHARMACEUTICAL COMPOSITIONS AND METHODS FOR THE TREATMENT AND PREVENTION OF CANCER

FIELD OF THE INVENTION

This invention relates to the field of cancer therapy. More specifically, it describes the use of cell extracts to form compositions for cancer treatment and prevention, and the use of cells to modify the compositions to achieve desired characteristics.

BACKGROUND OF THE INVENTION

The epigenome directs the genome to execute gene expression programs required for normal life. It comprises two different components: the chromatin structure, and a pattern of DNA methylation[1]. A gene can be found in different epigenetic states resulting from differences in histone modification and DNA methylation. Epigenetic modifications play an important role during normal development by regulating gene expression through stable activation or silencing of differentiation-associated genes. Unlike genetic changes, epigenetic changes do not alter the primary DNA sequence and are therefore reversible.

Collas et al[2] describe strategies for reprogramming somatic cells to pluripotency. More specifically, Collas describes how an extract of undifferentiated embryonic stem cells (ESC) can elicit pluripotency and differentiation plasticity in an otherwise more developmentally restricted cell type.

This procedure involves reversible permeabilization of a somatic cell, transient incubation of the permeabilized somatic cells with intracellular extracts of ESCs, and resealing of the somatic cells.

The reprogrammed ESC-like pluripotent cells may then be differentiated into a particular cell type, and then be used for treating a patient in need of that particular cell type.

Hendrix et al[3] show methods for altering the behavior of metastatic melanoma by employing embryonic stem cell-preconditioned 3 dimensional matrices.

WO/2008/014426 discloses methods of isolating compounds from the microenvironment of ESCs and using these compounds to treat and/or prevent the growth and/or dissemination of aggressive tumor cells in a patient. More specifically, the invention relates to the administration to the patient of inhibitors of Nodal activity, including, but not limited to, those that are exclusively produced by human ESCs.

Such compounds may be isolated from a substrate or a matrix, such as MATRIGEL, that was conditioned by human ESCs. WO/2008/014426 also provides methods for contacting tumor cells with a matrix, such as MATRIGEL, that comprises human ESCs or a matrix that has been preconditioned by human ESCs.

Ingber D. E.[4] raises the possibility of developing a tissue engineering approach to cancer therapy in which biologically-inspired materials that mimic the embryonic microenvironment are used to induce cancers to revert into normal tissues. It is further suggested that since physical factors may contribute to cancer formation, then biomaterials and scaffolds used for medical devices and tissue engineering applications could provide yet another modality for cancer therapy.

WO09/098698 discloses scaffolds prepared from cell extracts for use in conditions necessitating tissue/organ regeneration, repair or replacement.

Although many drugs are in use for cancer treatment, there is a desire for additional and more effective compositions and methods for cancer treatment and prevention. The present invention addresses this need.

SUMMARY OF THE INVENTION

The present invention is based on the understanding that the cellular and extracellular components of cells, and of stem cells in particular, in the form of extracts, can provide physical cues and serve as a rich source of biomolecules such as growth factors, cytokines, structural elements and transcription factors which are important to direct epigenetic reprogramming of cells and tissues, such as cancer cells and tissues. Accordingly, the present invention provides compositions that are made of various intracellular extracts and/or extracellular extracts for use in cancer treatment.

The present invention thus provides by a first of its aspects a pharmaceutical composition comprising a cell extract and a pharmaceutically acceptable carrier, for use in the treatment of a proliferative disease.

In one embodiment the pharmaceutical composition in accordance with the invention consists of a cell extract and a pharmaceutically acceptable carrier.

In one embodiment said proliferative disease is selected from the group consisting of neoplastic disorders, benign tumors and malignant tumors.

In certain embodiments, the cell extract is prepared from an animal cell or a plant cell. In a specific embodiment the animal cell is a mammalian cell. In one embodiment said mammalian cell is a human cell.

In certain embodiments the cell extract is prepared from a cell or a tissue selected from the group consisting of: a primary cell, a cultured cell, a cell line, an engineered tissue, and a primary tissue. Specifically, the cell extract is prepared from a cell selected from the group consisting of: stem cell, oocyte, egg cell, sperm cell, blastema cell, epithelial cell, neural cell, epidermal cell, keratinocyte, hematopoietic cell, melanocyte, chondrocyte, hepatocyte, B-cell, T-cell, erythrocyte, macrophage, monocyte, fibroblast, muscle cell, vascular smooth muscle cell, and a fibroblast.

The stem cell in accordance with the invention is selected from a group consisting of: embryonic stem cell, undifferentiated stem cell, pluripotent stem cell, lineage-restricted stem cell, precursor cell, somatic stem cell, terminally differentiated somatic stem cell, cells expressing one or more markers of multilineage differentiation potential, cells expressing one or more markers of pluripotent stem cells, hematopoietic stem cells, neural stem cells, mesenchymal stem cells, and embryonic germ cells.

In certain embodiments the cell extract is selected from the group consisting of a cytosolic extract, a cytoplasmic extract, a nuclear extract, a whole cell lysate, extracellular extract, whole tissue extract and mixtures thereof.

In a specific embodiment the cell extract is prepared from a cell which is cultured in a cell culture device capable of exerting mechanical forces onto the cultured cells and is having a patterned surface.

In another aspect, the present invention provides a method for producing a cell extract for use in the preparation of a pharmaceutical composition, comprising:
  (a) Obtaining cells or tissues;
  (b) Preparing extracellular extracts and/or intracellular extracts from said cells or tissues; and
  (c) formulating the extracellular extracts and/or intracellular extracts to obtain a composition suitable for administration;

wherein said composition is for use in the treatment of a proliferative disease.

In certain embodiments the cell extracts may be modified. In one such embodiment the method described above further comprises the following steps, between steps (b) and (c):
  (i) Seeding at least one type of cells on said extract;
  (ii) Eliminating the cells from the extract.

In another embodiment, the method described above further comprises the following steps after step (b):
  i. Preparing a scaffold from said extract;
  ii. Seeding at least one type of cells on the scaffold;
  iii. Eliminating the cells from the scaffold; and
  iv. Formulating the scaffold to obtain a composition suitable for administration.

In certain embodiments said proliferative disease is selected from the group consisting of neoplastic disorders, benign tumors and malignant tumors.

In certain embodiments said intracellular extracts are prepared from separate cellular compartments, selected from a group consisting of a cytosolic compartment, a cytoplasmic compartment, a nuclear compartment, and any combination thereof.

In one specific embodiment, prior to step (b), said cells or tissues are cultured in a cell culture device capable of exerting mechanical forces onto the cultured cells and is having a patterned surface.

In another specific embodiment said additional cell seeding is performed in a cell culture device capable of exerting mechanical forces onto the cultured cells and is having a patterned surface.

Said extracellular and/or intracellular extracts may be further combined with a tissue extract.

In certain embodiments the steps of seeding and eliminating the cells are repeated at least twice.

The invention further provides a pharmaceutical composition obtained by the methods described above.

The invention also provides a pharmaceutical composition comprising one or more biomolecules isolated from the cell extracts produced by the methods described above.

In another aspect, the present invention provides a method of treating a proliferative disease in a patient comprising administering to the patient an effective amount of the pharmaceutical compositions of the invention.

In certain embodiments said proliferative disease is selected from the group consisting of neoplastic disorders, benign tumors and malignant tumors.

In another aspect, the present invention provides a method of reprogramming a cancer cell, comprising contacting the cancer cell with an effective amount of the pharmaceutical composition of the invention wherein said composition modulates at least one component of a cellular pathway associated with cancer, thereby reprogramming the cancer cell.

DETAILED DESCRIPTION OF EMBODIMENTS

Epigenetic modifications play an important role during normal development by regulating gene expression through stable activation or silencing of differentiation-associated genes. Unlike genetic changes, epigenetic changes do not alter the primary DNA sequence and are therefore reversible.

Cancer can result from both epigenetic and genetic alterations of the genome, leading to activation of oncogenes and inactivation of tumor-suppressor genes. Epigenetic changes can promote cell proliferation, inhibit apoptosis, and induce angiogenesis during tumorigenesis. Whether a cell manifests a malignant phenotype or not is determined by its differentiation state and thus epigenetic conformation.

The present invention thus provides pharmaceutical compositions and methods for the treatment of proliferative diseases such as cancer, wherein the pharmaceutical compositions are composed of intracellular and/or extracellular extracts, preferably extracts of stem cells.

Without wishing to be bound by theory, the compositions of the invention induce epigenetic modifications which may alter or reverse the malignant nature of the cancer cell.

In one embodiment, the cell extract comprises the intracellular compartment of pluripotent stem cells. The pluripotent stem cells are preferably undifferentiated. Furthermore, the pluripotent stem cells are preferably of mammalian origin, more preferably of human origin.

The cell extracts may be obtained from primary cells, cell lines, cultured cells, primary tissue or engineered tissue prepared in vitro. The cultured cells can be cultured in standard culture plates or in a cell culture device capable of exerting mechanical forces onto the cultured cells and having a patterned surface. Such a device is capable of directing cell orientation and inducing mechanical stimulation thereon, for example, a device as disclosed in WO09/098698.

Without wishing to be bound by theory, the culture device provides an environment for cell growth which mimics the natural environment of cells and tissues, i.e. the animal body. The combination of mechanical stimulation and a nano-scale or micro-scale patterned topography has a significant effect on the organization, orientation, growth, maturation and function of cells and tissues, e.g. the transcriptional activity and other intra- and extracellular activities are potentiated, and enhanced levels of various biomolecules such as cytokines, and growth factors are produced thereby serving as a richer source for extract preparation.

In a specific embodiment, the present invention provides a method for producing a biologically active composition, comprising:
  (a) Obtaining cells or tissues; optionally culturing the cells prior to further use;
  (b) Preparing extracellular extracts and intracellular extracts from said cells or tissues; optionally said cellular extracts are prepared from separate cellular compartments, e.g. cytosolic fraction, cytoplasmic fraction or nuclear fraction;

The extracellular and intracellular extracts may be further modified.

In one specific embodiment, additional cells (optionally of the same or a different cell type) are cultured onto the extracellular extract and allowed to interact in a molecular, structural and functional way with the extracellular extract, e.g. to integrate newly synthesized biomolecules, thereby further modifying the extracellular extract. The modifying cells are then eliminated from the extracellular extract and the modified extracellular extract is then used for the preparation of the pharmaceutical composition.

In yet another specific embodiment, a scaffold is prepared from the extracellular or intracellular extracts. Additional cells (optionally of the same or a different cell type) are then cultured onto the scaffold and allowed to interact in a molecular, structural and functional way with the scaffold, e.g. to integrate newly synthesized biomolecules, thereby modifying the scaffold. The modifying cells are eliminated from the scaffold and the modified scaffold is then used for the preparation of the pharmaceutical composition.

The invention further encompasses biomolecules isolated from the extracts of the invention or from the modified extracts of the invention. These biomolecules may be individually isolated, or isolated in a manner that provides a group of factors in combination.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art. In the case where there are two or more definitions of a term which is used and/or accepted within the art, the definition of the term as used herein is intended to include all such meanings unless explicitly stated to the contrary.

Standard molecular biology techniques and procedures are generally performed according to conventional methods in the art e.g., Sambrook and Russell, 2001, Molecular Cloning, A Laboratory Approach, Cold Spring Harbor Laboratory Press, Cold Spring Harbor, NY; and Ausubel et al., 2002, Current Protocols in Molecular Biology, John Wiley & Sons, New York, N.Y.

The articles "a" and "an" are used herein to refer to one or to more than one (i.e., to at least one) of the grammatical object of the article. By way of example, "an element" means one element or more than one element.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, "administering" refers to the application of the composition of the present invention to a subject. Administration includes any means for applying the composition to a patient, including but not limited to through an oral route, a mucosal route, a parenteral route, a topical route, a transdermal route and a transcutaneous route, e.g. by injection. The composition may also be applied at tumor resection sites to prevent cancer recurrence.

The composition may target primary and metastatic tumor sites, where it would integrate into the local environment, and act to induce cancer reversal.

As used herein, "effective amount" and "therapeutically effective amount" are used interchangeably. The term "therapeutically effective amount" as used herein refers to a concentration or amount of a compound, material, or composition, as described herein, that is effective to achieve a particular biological result. Such results include, but are not limited to, the reprogramming of a cancer cell in the patient.

By "proliferative disease or disorder" is meant all neoplastic cell growth and proliferation, whether malignant or benign, including all transformed cells and tissues and all cancerous cells and tissues. Proliferative diseases or disorders include, but are not limited to, precancerous lesions, abnormal cell growths, benign tumors, malignant tumors, and "cancer."

As used herein, the term "malignancy" refers to a non-benign tumor or a cancer. As used herein, the term "cancer" connotes a type of proliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers include breast cancer, brain cancer, bladder cancer, prostate cancer, colon cancer, intestinal cancer, squamous cell cancer, lung cancer, stomach cancer, pancreatic cancer, cervical cancer, ovarian cancer, liver cancer, skin cancer, colorectal cancer, endometrial carcinoma, salivary gland carcinoma, kidney cancer, thyroid cancer, various types of head and neck cancer, and the like.

The method of the present invention may be used to treat premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976).

As used herein, the terms "composition" and "pharmaceutical composition" are used interchangeably and refer to a formulation suitable for administration into a patient, comprising as an active ingredient the extracts as disclosed herein and a pharmaceutically acceptable carrier.

The term "attached" as used herein encompasses interaction including, but not limited to, covalent bonding, ionic bonding, and mechanical interactions.

The term "biomolecule" refers to any molecule typically related to living organisms. This includes, for example, enzymes, receptors, nucleoproteins, neurotransmitters, hormones, cytokines, growth factors and chemotactic factors, antibodies, vaccines, haptens, toxins, interferons, ribozymes, anti-sense agents, plasmids, DNA, RNA, steroids, fatty acids, lipids, phospholipids, glycolipids, sterols, vitamins, lectins, carbohydrates, sugars, disaccharides, amino acids, nucleotides, phosphates, monosaccharides, peptides, peptide fragments, oligopeptides, neurotransmitters, polypeptides, proteins, nucleic acids, oligosaccharides, polysaccharides, secondary metabolites, lignins, and combinations thereof.

The term "differentiation factor" or "differentiation agent" as used herein, refers to a molecule that induces a stem cell or a progenitor cell to commit to a particular specialized cell type.

As used herein the term "Intracellular extract" refers to a preparation composed of a cytosolic extract, cytoplasmic extract, nuclear extract, a whole cell lysate or any combination thereof, wherein the extract comprises at least one biomolecule that is produced by the cells.

"Extracellular extract" refers to a preparation composed of at least one biomolecules that is secreted, excreted, released, or otherwise produced by cells or tissues, e.g. extracellular matrix, conditioned medium.

"Extracellular matrix" ("ECM") refers to one or more biomolecules that line the extracellular space around cells in vivo or in culture and support cell growth. Components of an extracellular matrix can include for example laminin, collagen, fibronectin and elastin.

A "conditioned medium" is a medium in which a specific cell, or population of cells or tissues has been cultured, and then removed. When cells or tissues are cultured in a medium, they may secrete biomolecules that can modulate epigenetic modifications in cancer cells. The medium containing the biomolecules is the conditioned medium.

"Growth factor" refers to a biomolecule that is effective to promote the growth of cells. For example, basic fibroblast growth factor (bFGF), acidic fibroblast growth factor (aFGF), epidermal growth factor (EGF), insulin-like growth factor I (IGF-I), insulin-like growth factor-II (IGF-II), platelet-derived growth factor (PDGF), vascular endothelial growth factor (VEGF), bone morphogenic proteins (BMPs), insulin, cytokines, chemokines, morphogens.

"Hydrogel" refers to a water-insoluble and water-swellable cross-linked polymer that is capable of absorbing at least 3 times, preferably at least 10 times, its own weight of a liquid.

As used herein, "scaffold" refer to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The term "isolated" refers to a material that is substantially or essentially free from components, which are used to produce the material. The lower end of the range of purity for the compositions is about 60%, about 70% or about 80% and the upper end of the range of purity is about 70%, about 80%, about 90% or more than about 90%. The term isolate can be used with reference to cells, polypeptides nucleic acids etc. Accordingly, an "isolated cell" refers to a cell which has been separated from other components and/or cells which naturally accompany the isolated cell in a tissue or mammal.

As used herein, "biocompatible" refers to any material, which, when implanted in a mammal, does not provoke an adverse response in the mammal A biocompatible material, when introduced into an individual, is not toxic or injurious to that individual, nor does it induce immunological rejection of the material in the mammal.

As used herein the term "injectable" refers to a form of a composition that is non-solid and may be injected into a subject. It encompasses, but is not limited to, a gel, a suspension or a solution, as well as a powder form amenable for rehydration.

As used herein "mammal" includes embryonic, juvenile, and adult mammals, unless the context clearly indicates otherwise. Mammals include, for example, humans, cows, sheep, big-horn sheep, goats, buffalos, antelopes, oxen, horses, donkeys, mule, deer, elk, caribou, water buffalo, camels, llama, alpaca, rabbits, pigs, mice, rats, guinea pigs, hamsters, dogs, cats, and primates such as monkeys.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "treat", "treating" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The terms can also mean prolonging survival as compared to expected survival if not receiving treatment. Those in need of treatment include those already with the condition or disorder as well as those prone to have the condition or disorder or those in which the condition or disorder is to be prevented.

"Proliferation" is used herein to refer to the reproduction or multiplication of similar forms, especially of cells. That is, proliferation encompasses production of a greater number of cells, and can be measured by, among other things, counting the number of cells, measuring incorporation of —H-thymidine into the cell, and the like.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "promoter" means a nucleic acid sequence which is required for expression of a gene product operably linked to the promoter. In some instances, this sequence may be the core promoter sequence and in other instances, this sequence may also include an enhancer sequence and other regulatory elements which are required for expression of the gene product. The promoter may, for example, be one which expresses the gene product in a tissue specific manner.

A "vector" is an agent which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acids into cells, such as, for example, polylysine compounds, liposomes, and the like. Examples of viral vectors include, but are not limited to, adenoviral vectors, adeno-associated virus vectors, retroviral vectors, and the like.

The term "patient" as used herein includes human and veterinary subjects. Veterinary subjects include both mammalian and non-mammalian animals.

As used herein, "embryo" refers to an animal in the prenatal early stages of growth and differentiation that are characterized by implantation and gastrulation, where the three germ layers are defined and established and by differentiation of the germs layers into the respective organs and organ systems. The three germ layers are the endoderm, ectoderm and mesoderm.

As used herein, a "stem cell" is a cell with the developmental potential to produce a more specialized cell type and at the same time to replicate itself. A stem cell may divide to produce two daughters that are themselves stem cells or it may divide to produce a daughter that is a stem cell and a daughter that is a more specialized cell type. A stem cell may originate from plants, mammals and non-mammal animals.

A "progenitor cell" or "precursor cell" is a cell which occurs in fetal or adult tissues and is partially specialized. It divides and gives rise to differentiated cells.

As used herein, a "pluripotent stem cell" is a stem cell with the developmental potential to produce all germ layer cell types, including ectodermal cell types, mesodermal cell types, and endodermal cell types.

An "embryonic stem cell" ("ESC") is a type of totipotent stem cell derived from a developing embryo. That is, it is a cell that can give rise to every cell type in a mammal. A totipotent stem cell is a type of "pluripotent stem cell". Embryonic stem cell-like (ESC-like) cell is totipotent stem cell not directly isolated from an embryo.

As used herein, "fetal cell" refers to a cell that is derived from a developing multi-cellular fetus.

As used herein, "germ cell" refers to a reproductive cell such as a spermatocyte or an oocyte, or a cell that will develop into a reproductive cell.

A "differentiated cell" is any cell with less developmental potential than a pluripotent stem cell.

As used herein, a "lineage-restricted stem cell" is a stem cell that can only give rise to cell types within one germ layer (i.e., to cell types within ectoderm or mesoderm or endoderm lineages). The lineage-restricted stem cell may have the potential to give rise to all cell types within the germ layer or it may only have the potential to give rise to a subset of cell types within the germ layer.

As used herein, a "pluripotent stem cell marker" is an mRNA or protein that is present in a pluripotent stem cell but absent in a lineage-restricted stem cell.

A "somatic stem cell" is a stem cell found in or isolated from a differentiated tissue, which can renew itself and give rise to at least one specialized cell type of the germ layer from which it originated. Non-limiting examples of somatic stem cells include "hematopoietic stem cells", "bone marrow mesenchymal stem cells", "neural stem cells", "epithelial stem cells", and "skin stem cells". "Hematopoietic stem cells" give rise to all the types of blood cells: red blood cells, B lymphocytes, T lymphocytes, natural killer cells, neutrophils, basophils, eosinophils, monocytes, macrophages, and platelets. "Bone marrow mesenchymal stem cells" give rise to a variety of cell types: bone cells (osteocytes), cartilage cells (chondrocytes), fat cells (adipocytes), and other kinds of connective tissue cells such as those in tendons. "Neural stem cells" in the brain give rise to its three major cell types: nerve cells (neurons) and two categories of non-neuronal cells—astrocytes and oligodendrocytes. "Epithelial stem cells" in the lining of the digestive tract occur in deep crypts and give rise to several cell types: absorptive cells, goblet cells, Paneth cells, and enteroendocrine cells. "Skin stem cells" occur in the basal layer of the epidermis and at the base of hair follicles. The epidermal stem cells give rise to keratinocytes, which migrate to the surface of the skin and form a protective layer. The follicular stem cells can give rise to both the hair follicle and to the epidermis.

A "somatic cell" is defined herein as a diploid cell of any tissue type that does not contribute to the propagation of the genome beyond the current generation of the organism. All cells except for germ cells are somatic cells and constitute the individual's body.

As used herein, the term "nuclear factor(s)" refers to proteins (or RNAs) normally bound within the nuclear membrane (except during mitosis in somatic cells and meiosis in germ cells). Nuclear factors may also include heteronuclear RNA ("hnRNA", i.e. messenger RNA prior to processing and export). The hnRNA may encode reprogramming factors. The nuclear factors may include DNA binding proteins bound in chromatin to the chromosomes, for example histones, transcription factors and other ancillary factors that may affect gene expression (either directly or indirectly).

The term "reprogramming" as used herein, refers to the step of altering or removing epigenetic modifications from the nucleus of a cell. Reprogramming facilitates a reduction in cell fate commitment and, thus, the differentiation state of the cell as a whole and in particular the nucleus. In essence, reprogramming consists of returning a cancer cell nucleus to a gene expression, epigenetic, and functional state characteristic of a non-cancerous cell.

The term "epigenetic modification" refers to the chemical marking of the genome. Epigenetic marks can include DNA methylation (imprints) as well as methylation and acetylation of proteins associated with DNA, such as histones. Parent-of-origin-specific gene expression (either from the maternal or paternal chromosome) is often observed in mammals and is due to epigenetic modifications. In the parental germlines, epigenetic modification can lead to stable gene silencing or activation. Other epigenetic modifications may include a change in epigenetic state, chromatin structure, transcription, mRNA splicing, post-transcriptional modification, mRNA stability and/or half-life, translation, post-translational modification, protein stability and/or half-life and/or protein activity of at least one component of a cellular pathway associated with cancer.

The terms "cell culture" and "culture" encompass the maintenance of cells in an artificial, in vitro environment. It is to be understood, however, that the term "cell culture" is a generic term and may be used to encompass the cultivation not only of individual cells, but also of tissues, organs, organ systems or whole organisms, for which the term "tissue culture" may occasionally be used interchangeably with the term "cell culture."

The terms "cell culture medium" or "culture medium" (plural "media" in each case) refer to a nutritive solution for cultivating cells and may be used interchangeably.

The term "oncogene" as used herein refers to a nucleic acid sequence encoding, or polypeptide, of a mutated and/or over-expressed version of a normal gene that in a dominant fashion can release the cell from normal restraints on growth. Oncogenes can alone or in concert with other changes or genes, contribute to a cells tumorigenicity. Examples of oncogenes include NRAS, KRAS, HRAS, MYC, MYCL1, MYCN, BCL2, BCL2L1, BCL2L2, TERT, VEGF, EGF, EGFR, ERBB3, GRB2, RAF1, ARAF, MAP2K2, MAPK1, MAPK3, MET, KIT, TP73L(AIX), CCND1, CDK4, MDM2, FES, FURIN, INSL3, CSF1R, MYBL2, MYB, PIK3CD, PIK3C2B, PIK3CG, PIK3R5, AKT1, HLIN-41, VDR, PXR, FOXA1, FOXA2, ASH1L, ARID1B, GR, GLI2, 14-3-3zeta, MO25, SMG1, FRAP1, PER2 and AKT3. A "proto-onco-gene" or "pro-oncogene" refers to the normal expression of a nucleic acid expressing the normal, cellular equivalent of an oncogene, typically these genes are usually a gene involved in the signaling or regulation of cell growth.

The term "tumor suppressor" refers to a nucleic acid sequence encoding, or polypeptide, that in its wildtype form has the ability to suppress, prevent, or decrease cell transformation. Tumor suppressor genes are genes that encode protein(s) that regulate cell growth and proliferation directly or indirectly, e.g. p53, Rb, and the like. If a tumor suppressor gene is damaged, it may lose its wildtype ability to regulate cell growth and proliferation, and the cells may become transformed or pre-disposed to transformation.

I—Tissues

Cells for use in accordance with the present invention may be isolated from various types of organs or tissues, and are not limited to any particular species or type of tissue, organ or cell. Cell can be obtained or recovered from prenatal tissues, postnatal tissues, and adult tissues. Preferably, cells are isolated from human organs or tissues.

Non limiting examples of tissues encompassed by the present invention are: prenatal tissues, postnatal tissues, and adult tissues, obtained for example from: skin (as a source, for example, of dermal fibroblasts, muscle, blood, blood vessels, bone, fat, bone-marrow, dental pulp, nervous tissue, cartilage, tendons, ligaments, placenta, or umbilical cord blood. Discarded tissues may also be used in accordance with the present invention, for example, foreskins and tissue obtained during esthetic or cosmetic surgical procedures.

The various types of tissue samples can be obtained for example from a biopsy including but not limited to a needle biopsy, a small wedge biopsy, lipoaspiration, or a partial/complete, excision/resection of organs, a cadaver (a deceased donor), or from disposed organ tissue e.g. an aborted fetus.

For example, skeletal muscle biopsies can be obtained easily from the arm, forearm, or lower extremities, and smooth muscle biopsies can be obtained from the area adjacent to the subcutaneous tissue throughout the body.

The biopsy can be readily obtained with the use of a biopsy needle, a rapid action needle which makes the procedure extremely simple and almost painless.

Cells may be obtained directly from the tissue or may be cultivated in culture prior to preparing an extract.

In one embodiment, the tissue or organ is cryopreserved and thawed prior to cell isolation and extract preparation.

Techniques for treatment of an organ or tissue to obtain cells are known to those skilled in the art (see, e. g. Freshney, Culture of Animal Cells. A Manual of Basic Technique, 2d Ed. A. R. Liss, Inc. New York, 1987, Ch. 9, pp. 107-126).

For example, the tissue or organ can be mechanically disrupted and/or treated with digestive enzymes or chelating agents to weaken the interactions between cells making it possible to obtain a suspension of individual cells.

Typically the method will include a combination of mechanical disruption, enzyme treatment and chelating agents. In one technique the tissue or organ is minced and treated simultaneously or subsequently with any of a number of digestive enzymes either alone or in combination.

Examples of enzymes useful in dissociating cells include, but are not limited to, trypsin, chymotrypsin, collagenase, elastase, hyaluronidase, DNase, pronase, dispase, liberase and the like. Mechanical disruption can also be accomplished by, for example, the use of blenders, sieves, homogenizers, pressure cells, and the like.

It is preferable to use mechanical disruption of the tissue through microsurgical/homogenization procedures well known in the art followed by enzymatic dispersion using collagenase at a concentration of 0.5 to 5 mg/ml, most preferably at 0.5 mg/ml, in suitable buffer such as phosphate-buffered saline either with or without added calcium, magnesium or EDTA. A most preferable embodiment involves mechanical disruption into tissue fragments that are at least 1 mm$^3$ in size followed by digestion in 0.5 mg/ml collagenase in PBS containing 1 raM EDTA, pH 7.2 to pH 7.5 at 37° C. for about 30 minutes. Other variations of this general method will be apparent to those skilled in the art and the present invention is not limited by the specific procedures used to generate dispersed tissue. Following enzymatic disruption, the enzymes used to prepare the dispersed tissue are washed out using a suitable solution such as phosphate-buffered saline followed by centrifugation by methods readily apparent to those skilled in the art.

The resulting suspension of cells and cell clusters can be further divided into populations of substantially homogenous cell types. This can be accomplished using standard techniques for cell separation including, for example, positive selection methods (e. g., clonal expansion and selection of specific cell types based on expression of specific cell surface markers), negative selection (e. g., lysis of unwanted cells), use of specific cell culture conditions, separation based upon specific gravity in a density solution (in density gradient centrifugation), differential adherence properties of the cells in the mixed population (differential adsorption), fluorescence activated cell sorting (FACS), immunomagnetic-based separation methods, and the like. Other methods of selection and separation are known in the art (see, e. g., Freshney, Culture of Animal Cells. A Manual of Basic Techniques, 2d Ed., A. R. Liss, Inc. New York, 1987, Ch. 11 and 12, pp. 137-168). Cells obtained by these methods are further expanded in culture using standard cell culture techniques known to those skilled in the art to obtain sufficient cell numbers as required for extract preparation.

Cell fractionation may be desirable, for example, when the donor has diseases such as cancer. A cell population may be sorted to separate malignant cells from normal noncancerous cells. The normal noncancerous cells isolated using one or more of the sorting techniques, may then be used for cell component extraction.

The tissue/organ is generally handled using standard sterile techniques preferably in a laminar flow safety cabinet. In the use and processing of all human tissue, the recommendations of the U.S. Department of Health and Human Services/Centers for Disease Control and Prevention should be followed (Biosafety in Microbiological and Biomedical Laboratories, Richmond, J. Y. et al., Eds., U.S. Government Printing Office, Washington, D.C. 3rd Edition (1993)). Preferably, the tissue is collected in a medium with antibiotics and antimycotic drugs and transported in ice. The tissue is cut into small pieces (e.g., 0.1×0.1 mm) using sterile surgical instruments.

Cells may also be isolated from samples of animal tissue obtained via biopsy, autopsy, donation, or other surgical or medical procedure.

II—Cells

In accordance with the invention, the cells may be autologous, allogeneic or xenogeneic with respect to the host or patient in need for the composition.

The cells of the invention can be obtained from any type of animal. In one embodiment, cells are isolated from a mammal In a preferred embodiment the cells are human cells. The cell extract may also be prepared from a plant cell.

The cell may be any cell type, including, for example, a differentiated cell, a precursor cell, or a stem cell. Some non-limiting examples include an epithelial cell (including oral and gastrointestinal mucosal epithelia, urinary tract epithelia), endothelial cell, vascular endothelial cell, neural cell, epidermal cell, keratinocyte, melanocyte, osteoblast, intervertebral disc cell, chondrocyte, hepatocyte, pancreatic cell, hematopoietic cell, angioblast, B-cell, T-cell, erythrocyte, macrophage, monocyte, bone marrow mesenchymal cell, fibroblast, myoblast, muscle cell, cardiomyocyte, amniotic or placental cell, oocyte, egg cell, an embryo cell, an ovary cell, sperm cell or stem cell. The invention also contemplates use of cells of established cell lines, for example, HeLa cells, FL cells, KB cells, HepG2 cells, WI-88 cells, MA104 cells, BSC-1 cells, Vero cells, CV-1 cells, BHK-21 cells, L cells, CHL cells, BAE cells, BRL cells, PAE cells, as well as genetically engineered cells.

The cell may be a stem cell. Types of stem cells include: undifferentiated stem cells, pluripotent stem cells, lineage-restricted stem cells, precursor cells, somatic stem cells, terminally differentiated somatic stem cells, cells expressing one or more markers of multilineage differentiation potential, cells expressing one or more markers of pluripotent stem cells, hematopoietic, neural, mesenchymal, postpartum, pancreatic, hepatic, retinal epithelial, olfactory bulb, endothelial, muscle, adipose-derived, ileac crest, bone marrow, periodontal ligament, oval and dermal stem cells and organ specific stem cells or progenitor cells, as well as blastema cells, embryonic stem cells, fetal stem cells, spermatogonial stem cells and embryonic germ cells.

In some cases the one or more pluripotent stem cell markers include one or more of OCT4, SOX2, UTF1, REX1, OXT2, NANOG, UTF1 AC133, CD9, DNMT3B, FOXD3, ALP, TERT, TERF, FZD9, GCNF, and SCGF.

In some cases the one or more markers are selected from a group consisting of a marker of adipogenic potential, osteogenic potential, neurogenic potential, chondrogenic potential, myogenic potential, and endothelial potential. Exemplary adipogenic markers include APOA2, APOD, APOE1 APOC1, and PPARG2. Exemplary osteogenic markers include BMP1, BMP2, OGN, and CTSK. Exemplary neurogenic markers include NTS, NRG1, MBP, MOBP, NCAM1, and CD56. Exemplary chondrogenic markers include COL4, COL5, COL8, CSPG2, and AGC1. Exemplary myogenic markers include MYF5, TMP1, and MYH 11. Exemplary endothelial markers include VWF and NOS.

In some cases wherein cells are stem cells said cells may express more than one marker which may be one or more of the following: Oct3/4, Sox2, SSEA-1 (−), SSEA-3 (+), SSEA-4 (+), TRA-1-60 (+), TRA-1-81 (+), lacZ and GFP. The stem cells may be human or non human cells and may possess telomerase activity and a chromosomal methylation pattern characteristic of pluripotential cells.

Pluripotent stem cells, such as human embryonic stem cells (hESCs) for use in the invention may be obtained from any established cell line. Examples of hESC lines that have been established include, but are not limited to, H1, H7, H9, H13 or H14 (available from WiCell established by the University of Wisconsin) (Thompson (1998) Science 282:1145); hESBGN-01, hESBGN-02, hESBGN-03 (BresaGen, Inc., Athens, Ga.); HES-I, HES-2, HES-3, HES-4, HES-5, HES-6 (from ES Cell International, Inc., Singapore); HSF-I, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-I and UCSF-2 (Genbacev et al., Fertil. Steril. 83(5): 1517-29, 2005); lines HUES 1-17 (Cowan et al., NEJM 350(13):1353-56, 2004); and line ACT-14 (Klimanskaya et al., Lancet, 365(9471): 1636-41, 2005). Embryonic stem cells used in the invention may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice (Takahashi et al, (2007) Cell 131(5):861; Yu et al., (2007) Science 318: 5858).

The cells as used herein may also be immunologically inert cells, such as embryonic or fetal cells, stem cells, and cells genetically engineered to avoid the need for immunosuppression.

In one embodiment, the cells are used immediately upon isolation. In another embodiment, the cells are cryopreserved, allowing their use in a cell bank.

In another embodiment the cells are expanded in culture for a defined period of time, prior to their use for extraction. The time period may be for example, 1-5 population doublings, 5-10 doublings, 10-20 doublings, 20-50 doublings, 50-100 doublings, or more than 100 doublings; alternatively, the period of time in culture may be defined as from 30 minutes to 1 hour, from 1 to 6 hours, from 6-12 hours, from 12-24 hours, from 1-7 days, from 7-30 days, or from 1-6 months and more.

For use in the present invention, cells can be plated directly onto the surface of culture vessels without attachment factors. Alternatively, the vessels can be precoated with natural, recombinant, or synthetic attachment factors or peptides (e.g., collagen or fibronectin, or fragments thereof).

Certain animal cells for culturing according to the present invention may be obtained commercially, for example from ATCC (Rockville, Md.), Cell Systems, Inc. (Kirkland, Wash.), Clonetics Corporation (San Diego, Calif.), BioWhittaker (Walkersville, Md.), or Cascade Biologicals (Portland, Oreg.).

The optimal plating and culture conditions for a given animal cell type can easily be determined by one of ordinary skill in the art using only routine experimentation.

In some cases genetically engineered cells are used, wherein at least one cell of the population of cells is transfected with an exogenous polynucleotide encoding a diagnostic or a therapeutic product which can assist in tissue healing, replacement, maintenance and diagnosis. Some non-limiting examples of such products include—cytokines, growth factors, chemokines, chemotactic peptides, tissue inhibitors of metalloproteinases, hormones, angiogenesis modulators either stimulatory or inhibitory, immune modulatory proteins, neuroprotective and neuroregenerative proteins and apoptosis inhibitors. Some specific exemplary proteins include erythropoietin (EPO), EGF, VEGF, FGF, PDGF, IGF, IFN-α, IFN-β, TGF-α, TGF-β, TNF-α, IL-1, BDNF, GDF-5, BMP-7 and IL-6. The desired gene product can be either constantly or transiently expressed.

In one embodiment, the cells are treated with one or more differentiation agents.

In another embodiment, the cells are treated with one or more epigenetic altering agents.

The cells of the invention can be cultured at all stages of cell cycle. The cells may also be cultured with one or more agents designed to maintain the cell actively in mitosis, for all or part of the time that the cell is maintained in culture. The cells may be exposed to a treatment designed to drive the cell into a particular stage of the cell cycle or to arrest the cell at a particular location in the cell cycle, such as the S, G1, M, or G2 phases, or in a metaphase to anaphase transition cell cycle phase. The cell cycle phase of the cell may be induced by a synchronisation agent. The synchronisation agent may for example be Nocodazole.

Extracts made from cells at a specific phase of the cell life-cycle can contain biomolecules that are preferentially present and active only during that particular phase. Cells collected from a single cell cycle phase can be expected to yield the maximal concentration of the particular biomolecule present only within that phase. For example, during M-phase (mitosis or meiosis) the nuclear envelope is broken down and nuclear and cytoplasm components are found within the same soluble cytosol at physiological concentrations and stoichiometry.

In another embodiment, the cells may be induced to exit the cell cycle and enter G0. Cells in G0 may be obtained directly upon isolation from the animal, or may be obtained from cells that were initially cycling in culture and were then induced to exit the cell cycle by, for example, removal of serum and mitogen factors.

In a specific embodiment, cells may be derived from an animal, expanded in culture as described above, and then induced to enter a particular stage of the cell cycle and stopped, such as G0. The cells may then be maintained in culture prior to the extraction step.

III—Cell Culture Conditions

Cells are typically cultivated in a cell incubator at about 37° C. The incubator atmosphere is humidified and contains about 3-10% carbon dioxide in air, although cultivation of certain cell lines may require as much as 20% carbon dioxide in air for optimal results. Culture medium pH is in the range of about 7.1-7.6, about 7.1-7.4, or about 7.1-7.3. Cells in closed or batch culture typically undergo complete medium exchange (i.e., replacing spent media with fresh media) every few days as required by the specific cell type, typically about every 2-3 days. Cells in perfusion culture (e.g., in bioreactors or fermentors) receive fresh media on a continuously recirculating basis.

Culture and differentiation agents useful in this invention include, by way of example, the following: medium refers to culture media for cells, as for example DMEM/F12 (Dulbecco's modified Eagle's medium/Ham's F12, 1:1, Invitrogen, Carlsbad, Calif.), also encompassing possible alternatives, variations and improvements equivalent to this cell culture medium. In accordance with the particular needs of the cultured cell, the medium may be supplemented with serum preferably at least 5% serum, and more preferably about 15% serum. According to a particular embodiment of the invention, said serum is from bovine origin, more particularly bovine fetal serum, although synthetic and non-synthetic serums, from human and other animals may also be employed, as well as other synthetic or natural reagents, including mixtures thereof, that allow the culture of the cells.

In some cases the medium is serum free medium. In some other cases the cell culture medium may contain antibiotics such as penicillin and streptomycin and/or amino acids such as glutamine and other non-essential amino acids and mixtures thereof. The cells as described herein may be cultured in the presence of a single agent or multiple agents, concurrently or sequentially, for a variable duration of time.

The choice of a specific medium depends on the type of cultured cell and is well within the knowledge of a person skilled in the art.

The medium according to the present invention may comprise a) base medium, b) supplements, and c) growth factors. The base medium may include commonly used formulations well known to those skilled in the art including: RPMI, other commonly used basal media and preferably MEM or more preferably the alpha modification of MEM ($\alpha$-MEM). These base medium also contain commonly used buffers to maintain physiological pH during the cell culture process, including but not limited to, sodium bicarbonate, HEPES and other buffer substances with a pKa in the physiological pH range. Supplements added to the base medium also include those commonly used in cell culture including transferrin or other iron-chelating agents, insulin (including natural or recombinant forms, insulin-like growth factors I & II, and related substances), trace elements, sodium pyruvate, non-essential amino acids, dextran at various molecular sizes, hydocortisone, ethanolamine, glucose and the tri-peptide, glycyl-histidine-lysine. The appropriate concentrations & compositions for such supplements will be readily apparent to those skilled in the art. Optimal levels of cell culture medium constituents are often determined through an empirical process of testing potential concentrations against a defined endpoint including for example, the growth rate of the cells, etc. The exact formulation of various basal medium supplements may be varied from the list of specific supplements described above while still retaining the specific characteristics of the present invention that primarily includes the ability to support growth of the mesenchymal cell culture. The concentrations and other ingredients in a formulation of standard cell culture medium are well known to those of ordinary skill in the art.

The present invention also contemplates the use of "defined culture media" or "serum-free media" (SFM). A number of SFM formulations are commercially available, such as those designed to support the culture of endothelial cells, keratinocytes, monocytes/macrophages, fibroblasts, chondrocytes, or hepatocytes, which are available from GIBCO/LTI (Gaithersburg, Md.). For example, SFM formulations supporting in vitro culture of keratinocytes have been reported (e.g. U.S. Pat. Nos. 4,673,649 and 4,940,666).

The culture media of the present invention are typically sterilized to prevent unwanted contamination.

The media used in accordance with the invention include components which are known to the skilled artisan or can be otherwise deduced using routine methods.

In another embodiment of the invention the cultured cells may be reinforced with exogenously added extracellular matrix proteins, e.g., collagen, laminin, fibronectin, vitronectin, tenascin, integrin, glycosaminoglycan (hyaluronic acid, chondroitin sulfate, dermatan sulfate, heparan sulfate, heparin, keratan sulfate and the like), elastin and fibrin. In some embodiments of the invention growth factors and/or cytokines, such as vascular endothelial cell growth factors, platelet derived growth factors, epidermal growth factors, fibroblast growth factors, hepatocyte growth factors, insulin-like growth factors, and transforming growth factors are exogenously added to the culture.

The cells may be cultured on a surface of glass, ceramic or a surface-treated synthetic polymer. For example, polystyrene that has been subjected to a surface treatment, like $\gamma$-ray irradiation or silicon coating, may be used as a surface for cell culture.

Cells which grow to over 85% confluence form cell sheet layer that may be separated from the surface either mechanically, or by using proteolysis enzymes, such as trypsin or dispase. Non-enzymatic cell dissociation could also be used. A non-limiting example includes a mixture of chelators sold under the tradename CELLSTRIPPER (Mediatech, Inc., Herndon, Va.), a non-enzymatic cell dissociation solution designed to gently dislodge adherent cells in culture while reducing the risk of damage associated with enzymatic treatments.

In another embodiment, cells are cultured on a non-adherent surface at sufficient densities. This provides a cell sheet layer that has only a few structural defects as they are recovered with intracellular desmosome structures and the cell-to-cell connectivity and orientation is being kept intact.

In another embodiment, cells are cultured on thermoresponsive dishes supplied for example, by CellSeed, Inc. (Tokyo, Japan).

In this embodiment, the culture surface can be inherently non-adherent or can be rendered non-adherent by surface coatings well known to those skilled in the art. Commercially available cell growth support devices include, for example, the range of Corning® Ultra Low Attachment surface cell culturing products (Corning Inc., Corning N.Y.). These products have a hydrogel layer that is hydrophilic and neutrally charged covalently bound to polystyrene surfaces. Since proteins and other biomolecules passively adsorb to polystyrene surfaces through either hydrophobic or ionic interactions, this hydrogel surface naturally inhibits nonspecific immobilization via these forces, thus inhibiting subsequent cell attachment. Other biocompatible non-adherent materials include ePTFE, polystyrene, stainless steel, and some cross-linked cellulose derivatives. Examples thereof include cross-linked hydroxyalkyl celluloses e.g. hydroxyethyl cellulose, hydroxypropyl cellulose, methyl, thyl and methyl thyl celluloses. Cross-linked carboxyalkyl celluloses also included are carboxymethyl cellulose cross-linked with ethylene glycol diglycidyl ether (EGDGE) or 1, 4 butanediol diglycidyl ether. Other materials include polyvinyl alcohol, poly (2-hydroxyethyl methacrylate) (Cellform® (MP Biomedicals, Irvine, Calif.), agarose, and crosslinked agarose.

Cells can also be seeded into or onto a natural or synthetic three-dimensional support matrix such as a preformed collagen gel or a synthetic biopolymeric material. Use of attachment factors or a support matrix with the medium of the present invention will enhance cultivation of many attachment-dependent cells in the absence of serum supplementation.

The cell seeding densities for each experimental condition can be selected for the specific culture conditions being used. For routine culture in plastic culture vessels, an initial seeding density of, for example, $1-5\times10^4$ cells per $cm^2$ is useful. In certain cases, micromass cultures are used.

IV—Cell Transfection and Transformation of Cells in Culture

In accordance with the invention cells may be genetically altered by the introduction of a heterologous nucleic acid (e.g. DNA), using various methods known in the art including calcium-phosphate- or DEAE-dextran-mediated transfection, protoplast fusion, electroporation, liposome mediated transfection, direct microinjection and adenoviral or retroviral infection.

In a specific embodiment, a calcium-phosphate precipitate containing DNA encoding the gene(s) of interest can be prepared using the technique of Wigler et al. ((1979) Proc. Natl. Acad. Sci. USA 76:1373-1376). Cultures of adult stem cells (e.g., liver stem cells or adipose stem cells) or their progeny are established in tissue culture dishes. Twenty-four hours after plating the cells, the calcium phosphate precipitate containing approximately 20 µg/ml of the heterologous DNA is added. The cells are incubated at room temperature for 20 minutes. Tissue culture medium containing 30 µM chloroquine is added and the cells are incubated overnight at 37° C. Following transfection, the cells are analyzed for the uptake and expression of the foreign DNA. The cells may be subjected to selection conditions that select for cells that have taken up and expressed a selectable marker gene.

Selectable marker genes include, but are not limited to GFP (green fluorescence protein) or a drug resistance gene. Some non-limiting examples of drug-resistance genes for use in the invention include hygromycin resistance gene, neomycin resistant gene, ampicillin resistance gene, E. coli gpt gene or the like.

In another specific embodiment, the heterologous DNA is introduced into a multipotent stem cell using the technique of retroviral transfection. Various processes are known in the art for transferring retroviral vectors into cultured cells. For example, recombinant retroviruses harboring the gene(s) of interest are produced in packaging cell lines to produce culture supernatants having a high titer of virus particles (for example, $10^5$-$10^6$ pfu/ml). The recombinant viral particles are used to infect cultures of the stem cells (e.g., adult liver stem cells or adult adipose stem cells) or their progeny by, for example, incubating the cell cultures with medium containing the viral particles and 8 µg/ml polybrene for three hours. Following retroviral infection, the cells are rinsed and cultured in standard medium. The infected cells are then analyzed for the uptake and expression of the heterologous DNA. The cells can be subjected to selective conditions that select for cells that have taken up and expressed a selectable marker gene. Since the gene transferred by the retroviral vector is integrated into chromosomal DNA of the host stem cell, the gene is transmitted to the daughter cell and therefore can be expressed stably over long period.

In certain embodiments the cells described herein, such as adult stem cells (e.g., liver stem cells or mesenchymal stem cells such as adipocyte stem cells), and/or derivatives thereof (e.g., hepatocytes, adipocytes, osteocytes, myoblasts, or chrondrocytes) are immortalized by transformation with an immortalizing gene or construct. Some non-limiting examples of useful immortalizing genes include myc, ras, SV40 T antigen, Ewing's sarcoma oncogene, hTERT, dominant-negative p53, dominant-negative Rb (retinoblastoma), adenovirus EIa, adenovirus EIb, papilloma virus E6, papilloma virus E7, bcr-abl, neu, ret and other immortalizing genes such as Notch.

The cells of the invention can be immortalized by transfection or transduction with a suitable vector, homologous recombination, or other appropriate techniques, so that they express an immortalizing activity (e.g., the telomerase catalytic component (TERT)).

In certain embodiments the immortalizing gene used in accordance with the present invention, or a selection gene, can be inserted between a pair of site-specific recombination sequences so that the gene can be excised when desired. Representative site-specific recombinant sequences include the LoxP sequence, the FRT sequence, or the like. The LoxP sequence is used for performing homologous recombination by the enzyme Cre recombinase.

V—Cell Differentiation and Characterization

Differentiation

In certain embodiments, the present invention encompasses the induction of differentiation of stem cells into specific cell types, such as epithelial cells, stromal cells, cardiac cells, bone cells and more. As is readily apparent to those skilled in the art, there are several methods known and under current development for the differentiation of stem/progenitor cell lines into differentiated target cell types. The present invention is not to be limited by the specific methods used to induce differentiation, but rather includes use of all such methods that are operationally defined as yielding the desired differentiation into a fully differentiated cell type.

For example, U.S. Pat. No. 6,596,274, and U.S. Pat. No. 5,811,094 disclose methods for cell differentiation.

Mesenchymal stem cells can be induced to differentiate into adipocytes, osteocytes, chondrocytes, myocytes, or neuronal cells (e.g., Blanat-Benard et al. (2004) Circ. Res. 94:223). Markers for mesenchymal stem cells and their differentiated cell types are known in the art, for example see Silva et al. (2003) Stem Cells 21:661.

In one specific embodiment, induction of differentiation includes incubating mesenchymal stem cells with a composition comprising IBMX, dexamethasone, indomethasone, and insulin, such that the cell differentiates into an adipocyte. Specifically, Adipocyte induction can be accomplished by culturing mesenchymal stem cells in a medium containing modified MEM with 10% FBS and supplemented with IBMX (I) (500 µM), dexamethasone (D) (1 µM), indomethacin (I) (1 µM), and insulin (I) (10 µg/ml) for three cycles of [IDI-I-2 days, insulin-1 day], and repeating the cycle three times. Successful induction of adipocytes can be determined using, e.g., Oil Red O staining of lipid vacuoles.

In yet another embodiment, the differentiation composition includes dexamethasone, L-ascorbate-2-phosphate, and β-glycerophosphate, such that the cell differentiates into an osteocyte. Specifically, induction of osteocyte differentiation is achieved by culturing stem cells in a medium composed of modified MEM with 10% FBS and supplemented with dexamethasone (0.1 µM), L-ascorbate-2-phosphate (50 µM), and β-glycerophosphate (10 mM) for about four weeks. Osteocytes can be identified by the presence of calcified extracellular matrix (ECM) using Von Kossa staining.

In yet another embodiment, the differentiation composition includes TGF-γ1, L-ascorbate-2-phosphate, and insulin, such that the cell differentiates into a chondrocyte. Specifically, chondrogenic differentiation can be achieved by culturing mesenchymal stem cells in micromass culture using a medium composed of modified MEM containing 10% FBS and supplemented with TGF-β1 (10 ng/ml), L-ascorbate-2-phosphate (50 µM), and insulin (6.25 µg/ml). Cells with characteristics of chondrocytes generally develop in about one week and can be identified, e.g., using Alcian blue (pH 1.0) staining, which detects the presence of proteoglycans.

Myogenic differentiation can be induced, e.g., by culturing mesenchymal stem cells in modified MEM containing 5% horse serum and supplemented with 50 µM hydrocortisone for four to six weeks. Differentiated cells can be identified, e.g., by immunostaining with an antibody that specifically recognizes skeletal myosin.

The methods of inducing differentiation that are described herein are exemplary and are not intended to be limiting. Other suitable methods of identifying specific differentiated cell types are known in the art and can be used to identify differentiated cells obtained from adult stem cells cultured using the methods described herein.

Characterization

The process of making a differentiated cell from a stem cell is accompanied by changes in the expression of cell markers. There are also unique pluripotent stem cells markers as well as markers of multilineage differentiation. Such cell markers are typically expressed as mRNA and/or protein. Detection of the mRNA or protein markers may be performed by any method known in the art. In some embodiments, nucleic acids and/or proteins will be isolated from the cells and then analyzed.

Tissue-specific protein markers can be detected using any suitable immunological technique such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium.

The expression of tissue-specific markers can also be detected at the mRNA level by Northern blot analysis, dot-blot hybridization analysis, or by reverse transcriptase initiated polymerase chain reaction (RT-PCR) using sequence-specific primers in standard amplification methods. See for example, U.S. Pat. No. 5,843,780. Sequence data for the particular markers can be obtained from public databases such as GenBank (URL www.ncbi.nlm.nih.gov/genbank/). Expression of tissue-specific markers as detected at the protein or mRNA level is considered positive if the level is at least 2-fold, and, in certain instances, more than 10- or 50-fold above that of a control cell, such as an undifferentiated adult liver stem cell, a fibroblast, or other unrelated cell type.

VI—Engineered Tissues

The present invention also contemplates use of engineered tissues as a source for preparing tissue and cell extract compositions. A variety of tissue engineering techniques are known, including tissue in-growth, seeding of cells on artificial or biodegradable scaffolds and collagen gels, and tissue "self-assembly". In the self-assembly method, cells are induced to secrete and organize an extracellular matrix and thereby form a sheet of living tissue. The self-assembly method takes advantage of the fact that cells such as fibroblasts can produce a suitable extracellular matrix when grown in the presence of ascorbic acid.

In a certain embodiment, when mesenchymal cells, such as mesenchymal stem cells, are cultured in a planar culture substratum using L-ascorbic acid or a phosphate derivative of L-ascorbic acid (e. g. Asc 2-P), serum, and growth factors, they show an abundant synthesis of extracellular matrix proteins. This creates the basis of the endogenous extracellular matrix. L-ascorbic acid plays an important role since it is a cofactor for the hydroxylation of proline and lysine residues in collagen, and also it increases both the rate of transcription of procollagen genes and stability of procollagen mRNA. The extracellular material is comprised of different proteins, such as collagen type I, other collagen types (fibrillar and non-fibrillar), elastin, fibrillin, glycosaminoglycans (such as decorin), growth factors, and glycoproteins.

An exemplary embodiment of methodology for generating such engineered tissues is described in U.S. Pat. No. 5,618,718 by Auger et al. In summary, Auger et al. describe that smooth muscle cells, at a concentration equivalent to $10^4$ cells/cm$^2$, are plated into 75 cm$^2$ sterile Petri dishes. Cell medium is supplemented with a 3:1 DMEM and Ham's F12 modified medium, fetal bovine serum, penicillin and gentamicin, and with an ascorbic acid solution. For example, a final ascorbic acid solution between 50-100 µg/ml can be used every other day. Culture conditions are kept at 92% air and 8% CO2 at full humidity. Culture time is approximately three weeks. At the end of the maturation time, the sheet of living tissue spontaneously detaches from the substratum.

It can be appreciated that a variety of methods can be used to prepare the sheets of living tissue and the present invention is not limited in scope by using one particular shape (i.e.

thickness and size), cell type, origin, age, maturation time, component concentration, and culture conditions to generate the sheet of living tissue.

To produce a sheet layer, a cell population (homogenous or heterogeneous) is cultured on a non-adherent substrate in the presence of commonly available culture media components, to promote extracellular matrix protein production. After an extended culture period, enough extracellular matrix protein is produced to make a coherent cell sheet.

Cells can be seeded at different densities sufficient to permit the formation of cell sheet layer. This will vary for different cell types and will need to be optimized. In the case of chondrocytes, the cell densities can range from 1,000 cells/$cm^2$ to 100,000 cells/$cm^2$.

Appropriate culture medium (for example, DMEM medium, MEM medium, HamF12 medium, HamF10 medium) is added. Cells of the required density are then added so that cells settle to the bottom of the dish. Alternatively cells of the required number can be suspended in the culture medium and added. In this case, cells will not attach to the bottom of the dish, and cell-to-cell adhesion creates cell sheet layer. Cultures are maintained for a few days to a few weeks before cell sheet layer can be recovered. During culture, the culture medium may be exchanged, if needed. Usually, the culture medium is exchanged every 0.6 to 2 days of the culture. The addition of agents that promote cell growth, viability and/or cell-to-cell adhesion can be used during the culture process. For example, addition of agents such as ascorbic acid, retinoic acid, and copper can be used to increase the production of extracellular matrix proteins thereby generating a more robust sheet layer. Growth factors capable of stimulation of extracellular matrix protein production could be used or a combination of growth factors, microelements, vitamins and such.

The tissue sheet may comprise any number of various cell types. Cells include, for example, embryonic stem cells and mesenchymal stem cells.

V—Extract Preparation

Extract preparation may be done by any suitable method known in the art.

According to certain embodiments, a first step in extract preparation is cell disruption, which may be performed using one of the following non-limiting options: enzyme digestion, homogenization, sonication, Bead mill, mincing, mechanical grinding with abrasive materials, French press, or detergents.

Extraction is typically performed in the presence of an extraction buffer (also referred to as extraction medium). The extraction buffer is designed for maintaining the structure and function of the extract components. This may be achieved by including ribonuclease inhibitors and/or protease inhibitors and reducing agents (e.g. antioxidants) in the buffer, by maintaining a defined pH, cation strength, and salt concentration, and by keeping the buffer at a cold temperature.

The inclusion of ribonuclease inhibitors and/or protease inhibitors in the buffer or the extract is aimed at preventing or minimizing degradation of RNAs and/or proteins by cellular ribonucleases and/or proteases.

The inclusion of antioxidants in the buffer or the extract, for example dithiothreitol (preferably at 0.5-5 mM) and/or 3-mercaptoethanol (preferably at 100-500 mM), is aimed at preventing or minimizing inactivation of factors through oxidation.

The buffer or the extract may also be supplemented with an agent which inhibits protein dephosphorylation, for example, glycerophosphate and/or vanadate. Addition of such an agent is aimed at preventing or minimizing inactivation of factors through protein dephosphorylation.

The buffer or the extract may be supplemented with an energy regeneration system/mix comprising creatine kinase (for example at 50-100 µg/ml) and/or creatine phosphate (for example at 10-20 mM) and/or ATP (for example at 1-2 mM) and/or GTP (for example at 1-2 mM) and/or $MgCl_2$ (for example at 1 mM). The energy regeneration mix supplements biochemical energy in vitro.

The buffer or the extract may be supplemented with an agent that stabilizes the extract and/or buffer, for example glycerol and/or sucrose (preferably at 5-50% v/v). Stabilizing the buffer or the extract refers both to the preparation stage and the storage period.

The extracts used in the present invention can be prepared from whole cells or tissues (including cells and extracellular matrix components), or from specific cellular compartments e.g. a cytoplasmic compartment or a nuclear compartment, and comprise amino acids, peptides, polypeptides, proteins, carbohydrates, lipids, nucleic acids, glycoproteins, lipoproteins, glycolipids, glycosaminoglycans, and proteoglycans. Proteins include for example, chromatin remodelling complexes, such as BRG1 or Brahma, HDACs, histone methyl transferases, histones acetyl transferases, hydroxylases, signalling molecules, and transcription factors, such as SP1. Lipid components may include phosphoinositides, such as PIP2, IP3, and IP4. Nucleic acids/nucleotides may include RNA, DNA, cAMP, cGMP.

Extracellular matrix components include but are not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, and proteoglycans.

In some embodiments the extract is compartmentalized prior to further use. For example, nuclear extract, cytoplasmic extract, or whole cell extracts may be used, as well as any combinations thereof. Any of these may be fractionated on density gradients.

A particular embodiment of the present invention is an extract comprising the intracellular compartment of pluripotent stem cells. The pluripotent stem cells are preferably undifferentiated. Furthermore, the pluripotent stem cells are preferably of mammalian origin, more preferably of human origin.

The intracellular compartmental extract is prepared according to methods well-known in the art; see e.g. WO/2002/097065. The extract may comprise other constituents which improve its function.

Nuclear factors may be obtained from a karyoplast isolated from the cell. Alternatively, the nuclear factors may be obtained from a nucleus isolated from the karyoplast or the cell.

The nuclear membrane of the cell, of the karyoplast or of the isolated nucleus may be disrupted to release nuclear factors. The nuclear membrane may be disrupted by sonication, by isotonic bursting, and/or by using a homogenizer, or by other methods known in the art.

The extract may be prepared from a cell which has been pre-treated with an agent that causes enucleation. For example the agent may be cytochalasin, preferably cytochalasin B or D. Such agents inhibit intermediate filament production and stabilization, thereby aiding release of the mitotic/meiotic spindle or nucleus from the cell.

The extract may be provided as enucleated whole cytoplasm. Alternatively, the extract may be provided as a derivative of the cytoplasm of the cell. In a further embodiment, the extract is provided as a derivative of an isolated karyoplast.

The extract and/or medium may be supplemented with an agent that stabilizes the extract and/or medium, for example glycerol and/or sucrose (preferably at 5-50% v/v). Stabilization may be during preparation of the extract and/or medium or during storage.

In a specific embodiment, the composition of the present invention can be prepared from a medium which is conditioned by the culturing of cells and tissues. Such a conditioned medium may comprise biomolecules secreted, excreted, released, or otherwise produced by cells and tissues. Such a conditioned medium, and combinations of any of the biomolecules comprised therein, may be used in order to reprogram a cancer cell. A conditioned medium can be prepared according to methods well-known in the art; see e.g. WO/2010/080364.

Chemically modified derivatives of the composition may be prepared by one skilled in the art, in view of the disclosures described herein. Derivatives may include molecules formed by the deletion of one or more naturally-attached chemical group, or they may be modified by the covalent attachment of one or more polymers. For example, the polymer selected is typically water-soluble so that the molecule to which it is attached does not precipitate in an aqueous environment, such as a physiological environment. The polymer may be of any molecular weight, and may be branched or unbranched. Included within the scope of suitable polymers is a mixture of polymers. Preferably, for therapeutic use of the end-product preparation, the polymer will be pharmaceutically acceptable.

VI—The Use of Cells for Modification of the Extract

In one embodiment of the invention, the extract is further seeded with one or more types of cell populations to allow said cells to interact in a molecular, structural and functional way with the extract, e.g. to modify the originally produced extract by secreting various soluble factors, thereby supplementing the extract with additional biomolecules. The modifying cells can be of any cell type known in the art. Preferably, the modifying cells are stem cells, more preferably the modifying cells are human stem cells.

In a preferred embodiment, about 5,000 cells to 500 million cells are suspended in medium and applied to each square centimeter of the culture surface. Preferably, between 50,000 and 50 million cells, and more preferably, between 50,000 and 5 million cells are suspended in media and applied to each square centimeter of culture surface. The extract is incubated under standard culturing conditions, such as, for example, 37° C., 5% CO2, for a period of time until the cells attach. It will be appreciated that the density of cells seeded onto the extract can be varied. Other seeding techniques may also be used depending on the composition and the cells. For example, the cells may be applied to the extract by vacuum filtration. Selection of cell types, and seeding of cells onto the extract, will be routine to one of ordinary skill in the art in light of the teachings herein.

In one embodiment, the extract is seeded with one population of cells. In another embodiment, the extract is seeded with two or more types of cells. In another embodiment, the extract is seeded on two sides with two different populations of cells. This may be performed by first seeding one side of the extract and then seeding on the other side. For example, the extract may be placed with one side on top and seeded. Then the extract may be repositioned so that a second side is on top. The second side may then be seeded with a second population of cells.

In addition, the cells may be cultured on the extract in the presence of agents that promote cellular proliferation and growth. Such agents include a number of growth factors that can be selected based upon the cell types present (non limiting examples include: keratinocyte growth factor (KGF); vascular endothelial cell growth factor (VEGF); platelet derived growth factor (PDGF); fibroblast growth factor (FGF); transforming growth factor (TGF) α, β, and the like; insulin; growth hormone; colony stimulating factors; erythropoietin; epidermal growth factor (EGF); and hepatic erythropoietic factor (hepatopoietin)). Serum, such as fetal bovine serum (FBS) or the like, can also provide some of these growth factors. In addition, agents such as ascorbic acid can be used to increase extracellular matrix production.

The modifying cells are subsequently substantially eliminated from the extract prior to further use to provide a cell-free composition enriched with biomolecules provided by the population of the modifying cells.

Cells may be eliminated from the seeded extract, for example by air-drying or lyopholization to kill the cells. Thermal shock, radiation, acoustic treatment, changes in pH, mechanical disruption, addition of toxins, detergents (SDS or triton x100), enzymes (RNAase, DNAase, protease, lipase), or solvents (alcohol, acetone, or chloroform) may also be used. In addition, treatment with hypotonic or hypertonic solutions, which have nonphysiological ionic strengths, can also promote the cell elimination process. See, for example, WO 9603093 and WO 9632905.

In another embodiment, the extract can go through one or more rounds of cell seeding (by seeding the same or different types of cells) followed by cell elimination.

The extract is modified by the seeded cells. This modification occurs at the structural and functional level and is a result of a dynamic interaction between the seeded cells and the extract. It includes for example integration of newly synthesized biomolecules. It may improve the physical and biological characteristics of the composition, as well as the matching of the composition to treat a specific patient, by seeding cells which are autologous to a patient.

Seeding can also be done by serially seeding several types of cells, or simultaneously by seeding a mixed population of several types of cells, followed by the elimination of the cells by any suitable technique.

VII—Pharmaceutical Composition and Administration of the Composition

A further aspect of the invention provides a pharmaceutical composition comprising an extract according to the first aspect of the invention in admixture with a pharmaceutically or veterinarily acceptable adjuvant, diluent or carrier.

In certain embodiments, a pharmaceutical composition useful in the methods of the invention may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18th Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the active ingredient of the composition. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions of the present invention comprise Tris buffer of about pH 7.0-8.5, or acetate buffer of about pH 4.0-5.5, and may further include sorbitol, sucrose, Tween-20 and/or a suitable substitute therefor. In certain embodiments of the invention, the composition may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the composition may be formulated as a lyophilizate using appropriate excipients such as sucrose. The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8. When parenteral administration is contemplated, the therapeutic compositions for use in this invention may be provided in the form of a pyrogen-free, parenterally acceptable aqueous solution comprising the composition in a pharmaceutically acceptable vehicle. A particularly suitable vehicle for parenteral injection is sterile distilled water in which the composition is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used to promote sustained duration in the circulation. In certain embodiments, implantable drug delivery devices may be used to introduce the composition.

Pharmaceutical compositions of the invention can be formulated for inhalation. In these embodiments, the compositions are advantageously formulated as a dry, inhalable powder. In preferred embodiments, the composition inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. The compositions that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the composition. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or more extract compositions in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving the composition of this invention in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et ah, 1983, Biopolymers 22:547-556), poly (2-hydroxyethyl-methacrylate) (Langer et ah, 1981, J. Biomed. Mater. Res. J__5: 167-277 and Langer, 1982, Chem. Tech. j__2:98-105), ethylene vinyl acetate (Langer et ah, supra) or poly-D(−)-3-hydroxybutyric acid (European Patent Application Publication No. EP 133,988). Sustained release compositions may also include liposomes that can be prepared by any of several methods known in the art. See e.g., Eppstein et ah, 1985, Proc. Natl. Acad. Sci. USA 82:3688-3692; European Patent Application Publication Nos. EP 036,676; EP 088,046 and EP 143,949, incorporated by reference. Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The composition of this invention can be admixed, encapsulated, conjugated or otherwise associated with other molecules, molecule structures or mixtures of compounds, for example, liposomes, receptor targeted molecules, oral, rectal, topical or other formulations, for assisting in uptake, distribution and/or absorption in a patient, using methods that are well known in the pharmaceutical arts.

The composition of this invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the composition in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the composition is mixed with an inert solid diluent, for example, calcium carbonate, calcium phosphate or kaolin, or as soft gelatin capsules wherein the composition t is mixed with water or an oil medium, for example peanut oil, liquid paraffin or olive oil.

Formulations for oral use may also be presented as lozenges.

Aqueous suspensions contain the composition in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the composition in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the composition in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

The pharmaceutical composition of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, flavoring and/or coloring agents. The pharmaceutical composition may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable compositions.

The composition may also be administered in the form of suppositories, e.g., for rectal administration of the composition. This can be prepared by mixing the composition with a suitable non-irritating excipient that is solid at ordinary temperatures but liquid at the rectal temperature and will therefore melt in the rectum to release the composition. Such materials include cocoa butter and polyethylene glycols. The composition may be administered parenterally in a sterile medium. The composition, depending on the vehicle and concentration used, can either be suspended or dissolved in the vehicle. Advantageously, adjuvants such as local anesthetics, preservatives and buffering agents can be dissolved in the vehicle.

The composition can also be preferably applied as a topical gel, spray, ointment or cream, or as a suppository, containing a total amount of, for example, 0.075 to 30% w/w, preferably 0.2 to 20% w/w and most preferably 0.4 to 15% w/w. When formulated in an ointment, the composition may be employed with either paraffinic or a water-miscible ointment base.

Alternatively, the composition of this invention may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the composition through the skin or other affected areas. Examples of such dermal penetration enhancers include dimethylsulfoxide and related analogs.

The composition of this invention can also be administered by a transdermal device. Preferably topical administration will be accomplished using a patch either of the reservoir and porous membrane type or of a solid matrix variety. In either case, the composition is delivered continuously from the reservoir or microcapsules through a membrane into the composition permeable adhesive, which is in contact with the skin or mucosa of the recipient. If the composition is absorbed through the skin, a controlled and predetermined flow of the composition is administered to the recipient. In the case of microcapsules, the encapsulating agent may also function as the membrane. The transdermal patch may include the composition in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the composition of this invention is ordinarily combined with one or more adjuvants appropriate to the indicated route of administration. If administered by mouth, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of the composition in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The composition may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 14 g per patient per day). The amount of the composition that may be combined with the carrier materials to produce a single dosage form will vary depending upon the host treated and the particular mode of administration. Dosage unit forms will generally contain between from about 1 mg to about 500 mg of an active ingredient of the composition. The daily dose can be administered in one to four doses per day. In the case of skin conditions, it may be preferable to apply a topical preparation of the composition of this invention to the affected area two to four times a day.

It will be understood, however, that the specific dose level for any particular patient will depend upon a variety of factors including the activity of the specific composition employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Dosing frequency will depend upon the pharmacokinetic parameters of the particular composition used in the formulation. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

In certain embodiments, the pharmaceutical compositions can be administered alone or in combination with other therapeutic agents, in particular, in combination with other chemotherapeutic agents.

In another embodiment, the composition further includes at least one additional therapeutic agent. The therapeutic agent can be an analgesic, anesthetic, anti-rejection agent, or anti-tumor agent including but not limited to a chemotherapeutic agent, an anti-cell proliferation agent or any combination thereof.

The additional chemotherapeutic agent suitable for use with the composition is not limited to any particular agent. For example, any conventional chemotherapeutic agents of the following non-limiting exemplary classes may be incorporated into the composition: alkylating agents; nitrosoureas; antimetabolites; antitumor antibiotics; plant alkyloids; taxanes; hormonal agents; and miscellaneous agents.

Representative examples of the anticancer agent that may be administered in conjunction with the composition of the present invention include, but are not limited to, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2-specific inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium;

sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

The composition according to one exemplary embodiment of the present invention is administered in conjunction with therapeutics widely used to cure, prevent or treat cancer. Examples of the conventional therapeutics include, but are not limited to, surgery, chemotherapy, radiotherapy, hormone therapy, biological therapy and immunotherapy.

VIII. Diseases, Disorders or Conditions

As used herein the term "proliferative disorder" relates to diseases characterized by abnormal cell proliferation, for example cancer. The term "cancer" used in this application includes, but is not particularly limited to, solid tumor and blood-born tumor. The term "cancer" refers to a disease in skin tissues, organs, blood and blood vessels, which include, but is not particularly limited to, such cancers as bladder, bone or blood, brain, breast, cervix, chest, colon, endrometrium, esophagus, eye, head, kidney, liver, lymph node, lung, mouth, neck, ovary, pancreas, prostate, rectum, stomach, testicles, throat and uterus. The certain cancer includes, but is not particularly limited to, advanced malignancy, amyloidosis, neuroblastoma, meningioma, hemangiopericytoma, multiple brain metastase, glioblastoma multiformis, glioblastoma, brain stem glioma, poor prognosis malignant brain tumor, malignant glioma, recurrent malignant glioma, anaplastic astrocytoma, anaplastic oligodendroglioma, neuroendocrine tumor, adenocarcinoma, Dukes C & D colorectal cancer, unresectable colorectal cancer, metastatic hepatocellular carcinoma, Kaposi's sarcoma, karotype acute myeloblastic leukemia, Hodgkin's lymphoma, Non-Hodgkin's lymphoma, cutaneous T-cell lymphoma, cutaneous B-cell lymphoma, diffuse large B-Cell lymphoma, low grade follicular lymphoma, malignant melanoma, malignant mesothelioma, malignant pleural effusion mesothelioma syndrome, intraperitoneal carcinoma, papillary serous carcinoma, gynecologic sarcoma, soft tissue sarcoma, scelroderma, subcutaneous vasculitis, Langerhans' cell histiocytosis, leiomyosarcoma, fibrodysplasia ossificans progressive, hormone refractory prostate cancer, resected high-risk soft tissue sarcoma, unresectable hepatocellular carcinoma, Waldenstroms macroglobulinemia, smoldering myeloma, indolent myeloma, salpinx cancer, androgen-dependent prostate cancer, androgen-dependent stage IV non-metastatic prostate cancer, hormone-insensitive prostate cancer, chemotherapeutic-insensitive prostate cancer, papillary thyroid carcinoma, follicular thyroid carcinoma, medullary thyroid carcinoma, and leiomyoma, and head and neck cancer.

IX. Reprogramming Cancer Cells

Without wishing to be bound by theory the present invention provides a method for reprogramming a cancer cell, comprising contacting the cancer cell with the compositions of the invention which comprise one or more cell extract as described herein. Said compositions are capable of modulating at least one component of a cellular pathway associated with cancer, thereby reprogramming the cancer cell.

The modulation may comprise a change in the epigenetic state of the cell, its chromatin structure, transcription, mRNA splicing, post-transcriptional modification, mRNA stability and/or half-life, translation, post-translational modification, protein stability and/or half-life and/or protein activity of at least one component of a cellular pathway associated with cancer.

These components are selected from oncogenes, tumor suppressor genes and any other cancer-related genes known in the art.

The cancer-related genes may include any gene of the following list: ABL1, ABL2, AP15Q14, AF1Q, AF3p21, AF5q31, AKT, AKT2, ALK, ALO 17, AML1, API, APC, ARHGEF, ARHH, ARNT, ASPSCR1, ATIC, ATM, AXL, BCL1O, BCL1 IA, BCL1 IB, BCL2, BCL3, BCL5, BCL6, BCL7A, BCL9, BCR, BHD, B1RC3, BLM, BMPR1A, BRCA1, BRCA2, BRD4, BTG1, CBFA2T1, CBFA2T3, CBFB, CBL, CCND1, c-fos, CDH1, c-jun, CDK4, c-kit, CDKN2A-p14ARF, CDKN2A-p161NK4A, CDX2, CEBPA, CEP1, CHEK2, CHIC2, CHN1, CLTC, c-met, c-myc, COL1A1, COPEB, COX6C, CREBBP, c-ret, CTNNB1, CYLD, D10S170, DDB2, DDIT3, DDX1O, DEK, EGFR, EIF4A2, ELKS, ELL, EP300, EPS 15, erbB, ERBB2, ERCC2, ERCC3, ERCC4, ERCC5, ERG, ETV1, ETV4, ETV6, EVI1, EWSR1, EXT1, EXT2, FACL6, FANCA, FANCC, FANCD2, FANCE, FANCF, FANCG, FEV, FGFR1, FGFR1OP, FGFR2, FGFR3, FH, FIP1L1, FLI1, FLT3, FLT4, FMS, FNBP1, FOXO1A, FOXO3A, FPS, FSTL3, FUS, GAS7, GATA1, GIP, GMPS, GNAS, GOLGA5, GPC3, GPHN, GRAF, HEI1O, HER3, HIP1, HIST1H4I, HLF, HMGA2, HOXA11, HOXA13, HOXA9, HOXC13, HOXDI1, HOXD13, HRAS, HRPT2, HSPCA, HSPCB, hTERT, IGHα, IGKα, IGLα, IL21R, IRF4, IRTA1, JAK2, KIT, KRAS2, LAF4, LASP1, LCK, LCP1, LCX, LHFP, LMO1, LMO2, LPP, LYL1, MADH4, MALT1, MAML2, MAP2K4, MDM2, MECT1, MEN1, MET, MHC2TA, MLF1, MLH1, MLL, MLLT1, MLLT1O, MLLT2, MLLT3, MLLT4, MLLT6, MLLT7, MLM, MN1, MSF, MSH2, MSH6, MSN, MTS1, MUTYH, MYC, MYCL1, MYCN, MYH11, MYH9, MYST4, NACA, NBS1, NCO A2, NCOA4, NF1, NF2, NOTCH1, NPM1, NR4A3, NRAS, NSD1, NTRK1, NTRK3, NUMA1, NUP214, NUP98, NUT, OLIG2, p53, p27, p57, p16, p21, p73, PAX3, PAX5, PAX7, PAX8, PBX1, PCM1, PDGFB, PDGFRA, PDGFRB, PICALM, PM1, PML, PMS1, PMS2, PMX1, PNUTL1, POU2AF1, PPARG, PRAD-I, PRCC, PRKAR1A, PRO1073, PSIP2, PTCH, PTEN, PTPN11, RAB5EP, RAD51L1, RAF, RAP1GDS1, RARA, RAS, Rb, RB1, RECQL4, REL, RET, RPL22, RUNX1, RUNXBP2, SBDS, SDHB, SDHC, SDHD, SEPT6, SET, SFPQ, SH3GL1, SIS, SMAD2, SMAD3, SMAD4, SMARCB1, SMO, SRC, SS 18, SS 18L1, SSH3BP1, SSX1, SSX2, SSX4, Stathmin, STK11, STL, SUFU, TAF15, TALI, TAL2, TCF1, TCF12, TCF3, TCL1A, TEC, TCF12, TFE3, TFEB, TFG, TFPT, TFRC, TIF1, TLX1, TLX3, TNFRSF6, TOP1, TP53, TPM3, TPM4, TPR, TRAα, TRBα, TRDα, TRIM33, TRIP11, TRK, TSC1, TSC2, TSHR, VHL, WAS, WHSC1L18, WRN, WT1, XPA, XPC, ZNF145, ZNF198, ZNF278, ZNF384, and ZNFN1A1.

For further elaboration of general techniques useful in the practice of this invention, the practitioner can refer to standard textbooks and reviews in cell and tissue culture, embryology, and molecular biology. General techniques in cell culture and media collection are outlined in Large Scale Mammalian Cell Culture (Hu et at., Curr. Opin. Biotechnol. 8:148, 1997); Serum-free Media (K. Kitano, Biotechnology 17:73, 1991); Large Scale Mammalian Cell Culture (Curr. Opin. Biotechnol. 2:375, 1991); and Suspension Culture of Mammalian Cells (Birch et al., Bioprocess Technol. 19:251, 1990). Textbooks on the subject include General Techniques in Cell Culture (Harrison & Rae, Cambridge, 1997); Animal Cell Culture Methods (Barnes & Mather, eds., Academic Press, 1998); Culture of Animal Cells (I. Freshney, 4th.ed., John Wiley & Sons, 2000); Guidebook to the Extracellular Matrix, Anchor, and Adhesion Proteins (Kreis & Vale, eds., Oxford, 1999); Handbook of Cellular Manufacturing Systems (S. A. Irani, ed., John Wiley & Sons, 1999). The properties, culture, and differentiation of embryonic stem cells are described in Teratocarci nomas and embryonic stem cells: A practical approach (E J. Robertson, ed., IRL Press Ltd. 1987); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., al., 1993). Differentiation of stem cells is reviewed in Robertson, Meth. Cell Biol. 75:173, 1997; and Pedersen, Reprod. Feral. Dev. 10:31, 1998. References that further describe the culturing of particular cell types are listed further on in the disclosure.

General biochemical techniques are described in Short Protocols in Molecular Biology (Ausubel et al., eds., 4th ed. 1999). Methods of protein chemistry are described generally in Protein Methods (Bollag et al., 1996); Guide to Protein Purification (Deutscher et al., eds., Methods Enzymol. vol. 182, Academic Press, 1997); Protein Analysis and 5 Purification (L M. Rosenberg, Springer Verlag, 1996).

EXAMPLES

Example 1

Preparation of Extracellular Extract Composition (I)

Materials and Methods

Isolating and Culturing of Human Amniotic Fluid-Derived Mesenchymal Stem Cells (AF-MSCs)

Human AF-MSCs are isolated by the following method or by any other suitable method known in the art.

Amniotic fluid samples are obtained by amniocentesis performed between 16 and 20 weeks of gestation during routine prenatal diagnoses. Samples are analyzed to have normal karyotypes before further use. Then the samples are centrifuged at 400 g for 15 minutes. The pellet is resuspended in 2 mL of growth medium consisting of low-glucose Dulbecco's modified Eagle's medium (Invitrogen) supplemented with 20% FBS (Invitrogen), 5 ng/mL basic fibroblast growth factor (Peprotech), 10,000 U/mL of penicillin G sodium (Fisher), and 10 mg/mL of streptomycin (Fisher). The cells are plated in tissue culture flasks and incubated at 37 C with 5% humidified CO2 for 2-3 days, and then all nonadherent cells are discarded, and fresh medium is added. The medium is then replaced every 2-3 days until the cells reach 70% confluence, then they are treated with 0.25% trypsin, collected and replated in a split ratio of 1:3 under the same culture conditions.

Step 1: Seeding Cells

In order to facilitate extracellular matrix formation and induce alignment of cells and provide mechanical cues, cells can be seeded and grown on a device designed to recapitulate some of the native micro-environmental cues required for the growing of cells and formation of tissues. Details of an exemplary device are described in WO09/098698. Alternatively, cells can be grown on standard tissue culture plates or by any other method known in the art.

Cultured AF-MSCs are harvested using 0.25% trypsin-EDTA to detach the cells from the culture flasks. Trypsin is subsequently neutralized with growth medium. Cells are then pelleted at approximately 500 g, resuspended in fresh growth medium, counted with a hemocytometer, seeded onto the silicone substrate of the culture device at a density of $5 \times 10^4$ cells/cm$^2$. After incubation of 20-40 minutes allowing cells to attach, a pre-defined training program is initiated to apply a uniform cyclic strain of 2-4%, at a 0.2 Hz frequency. Culture medium is changed every 3-4 days. Following a period of approximately two weeks (time may change between different types of cultured cells) a layer of tissue is formed and the training program is stopped. Tissue formation is verified by histological analysis, and by using scanning electron microscopy imaging.

Step 2: Preparation of Extracellular Extract Composition

The silicone culture substrate with the grown layer of bone marrow derived mesencymal stem cells are transferred to a sterile hood and washed in PBS containing a protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation. The wash is repeated three times. Verification of cell removal and evaluation of the extracellular matrix (ECM) composition is done by histological analysis, scanning electron microscopy imaging and by SDS-PAGE and Western blotting. The resultant ECM composition can be freeze-dried and cut manually using a scalpel, or fragmented using a freezer mill, and then solubilized and formulated into an injectable hydrophilic composition or to any other formulation, suitable for administration into a patient in need of that composition, for the prevention and treatment of cancer. The following alternative method that is known in the art, (see U.S. Pat. No. 4,829,000) can also be used:

The layer of engineered tissue is washed and homogenized in ice cold 3.4M NaCl buffer supplemented with a protease inhibitor cocktail (0.5 mM PMSF, 2 mM EDTA, 0.1M EACA, 2 mM NEM and the like). The homogenate is then centrifuged at 10,000 rpm at 4° C. for 15 minutes, following which the supernatant is discarded and pellets are resuspended in the 3.4M NaCl buffer. This step is repeated 2-3 times. Pellets are then resuspended in a 2M urea buffer, homogenized and stirred overnight at 4° C. Then the extract is centrifuged at 14,000 RPM at 4° C. for 30 minutes and the supernatant is reserved. Pellets are re-homogenized in half the original volume of 2M urea buffer then the centrifugation step is repeated. The supernatant is then combined with the previously reserved supernatant. Then the combined extract is dialyzed in 0.05 M Tris-saline buffer with chloroform (for sterilization) for two hours in 4° C. then it is dialyzed in Tris-saline buffer several times, followed by DMEM. Then the extract is aliquoted into sterile tubes and stored in liquid nitrogen, or solubilized and formulated into an injectable hydrophilic composition, or to any other formulation, suitable for administration into a patient in need of that formulation, for the prevention and treatment of cancer.

Example 2

Preparation of Extracellular Extract Composition (II)

Materials and Methods

Culturing of Bone Marrow-Derived Mesenchymal Stem Cells

Human Mesenchymal Stem Cells (MSCs) are purchased from Lonza (Poetics Cat. PT-2501, Lonza, Basel, Switzerland) and are propagated in Mesenchymal Stem Cell growth medium (MSCGM; Lonza). The cells are maintained at 37° C. in a 5% CO2 incubator. The cells are seeded at 5,000 cells per cm$^2$ in T-flask, expanded for 3 to 4 days and at 70% confluency, harvested with trypsin, collected, and centrifuged at 300 rcf (relative centrifugal force) for 5 minutes. The trypsin/media are removed by aspiration and cells are washed three times with phosphate buffered saline (PBS).

Alternatively, MSCs can be isolated from bone marrow samples using the following method:

Bone marrow aspirate is obtained from the iliac crest of normal donors. The sample is transferred to a 50 ml sterile tube and supplemented with 20 ml of Hank's saline solution at +40 C. The tube is centrifuged at approximately 1000 rpm for 5 minutes to pellet the cells and to eliminate the supernatant and the lipid layer, which are then aspirated. Then the pellet is loaded onto Percoll or Ficoll type gradients (Sigma), centrifuged at 500 g for 15 minutes, after which the upper, low-density cell fraction containing mesenchymal cells is collected and plated for further expansion. Cells are cultured in alpha-MEM medium supplemented with 10% fetal bovine serum and 100 units/ml penicillin/streptomycin at 370 C in humidified atmosphere containing 95% air and 5% CO2. After one day, nonadherent cells are removed from the cultures by replacing the original medium with fresh medium. Subsequent medium changes are performed every 3-5 days. When culture dishes become confluent, the cells are detached using 0.25% trypsin containing 0.1 mM EDTA (GIBCO) for 10-15 minutes at 370 C. The action of trypsin is stopped with ½ volume fetal bovine serum. The cells are counted, split 1:3, and replated. Cells are resuspended in a 10% DMSO cryopreservation solution and cryopreserved in liquid nitrogen, or immediately used.

Isolating and Culturing of Human Umbilical Cord-Derived Mesenchymal Stem Cells (UC-MSCs)

Human umbilical cords from both sexes are obtained after full-term births with informed consent of the mother after either cesarean section or normal vaginal delivery, and aseptically stored at 4° C. in sterile saline until processing. Then, cord blood is drained and vascular tissue is removed, and the umbilical cords are finely minced, plated in tissue culture plates, and maintained in defined media composed of Dulbecco's modified Eagle medium (DMEM; Invitrogen) and MCDB-201 medium (Sigma) supplemented with 2% fetal bovine serum (FBS, HyClone), X1 insulin-transferrin-selenium (ITS, Invitrogen), 10 ng/mL of recombinant human epidermal growth factor, and 10 ng/mL of human platelet-derived growth factor BB (R&D Systems, Inc.). After 1 week in culture, cord remnants are removed and the attached cells were maintained in defined media. At 70% confluency, cells are harvested with trypsin, collected, and centrifuged at 300 rcf for 5 minutes. The trypsin/media are removed by aspiration and cells are washed three times with phosphate buffered saline (PBS).

Culturing of Human Embryonic Stem Cells (hESCs)

Human Embryonic Stem Cells (hESCs) are cultured essentially as described in the art. Briefly, hESCs are routinely cultured on inactivated mouse embryonic fibroblast (MEF) feeder cells in KnockOut DMEM (Gibco) supplemented with 20% KnockOut Serum Replacement (Gibco), 2 mM L-glutamine (L-Glu, Gibco), 0.1 mM 2-mercaptoethanol (Gibco), 1% nonessential amino acids (Gibco), and 4 ng/ml basic fibroblast growth factor (Invitrogen). Cells are split at the ratio of 1:10-1:12 every 4-5 days by using 1 mg/ml collagenase type IV.

Step 1: Seeding Cells

In order to facilitate extracellular matrix formation and induce alignment of cells and provide mechanical cues, cells can be seeded and grown on a device designed to recapitulate some of the native micro-environmental cues required for the growing of cells and formation of tissues. Details of an exemplary device are described in WO09/098698. Alternatively, cells can be grown on standard tissue culture plates or by any other method known in the art.

Cultured bone marrow-derived MSCs are harvested using 0.25% trypsin-EDTA to detach the cells from the culture plates. Trypsin is subsequently neutralized with growth medium. Cells are then pelleted at approximately 500 g, resuspended in fresh growth medium, counted with a hemocytometer, seeded onto the silicone substrate of the culture device at a density of $5\times10^4$ cells/cm$^2$. After incubation of 20-40 minutes allowing cells to attach, a pre-defined training program is initiated to apply a uniform cyclic strain of 2-4%, at a 0.2 Hz frequency. Culture medium is changed every 3-4 days. Following a period of approximately two weeks (time may change between different types of cultured cells) a layer of tissue is formed and the training program is stopped. Tissue formation is verified by histological analysis, and by using scanning electron microscopy imaging.

Step 2: Preparation of Extracellular Extract

The silicone culture substrate with the grown layer of bone marrow-derived MSCs are transferred to a sterile hood and washed in PBS containing a protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation. The wash is repeated three times. Verification of cell elimination and evaluation of the extracellular matrix (ECM) extract is done by histological analysis, scanning electron microscopy imaging and by SDS-PAGE and Western blotting. The resultant ECM extract can manually removed from the culture plates, be freeze-dried and cut manually using a scalpel, or fragmented using a freezer mill, and then solubilized and formulated into an injectable hydrophilic composition or to any other suitable formulation.

Step 3: Modification of the Extracellular Extract

The ECM extract of Step 2 can be further modified by incubation with any desired type of cells to achieve a desired characteristic of the extract. One to more type of cells can be consecutively used for the modification step In order to modify the extract, cultured cells (such as for example, UC-MSCs or hESCs) are harvested using 0.25% trypsin-EDTA to detach the cells from the culture plates, which is subsequently neutralized with growth medium. Then cells are pelleted at approximately 200 g, resuspended in fresh growth medium, counted with a hemocytometer and seeded in the culture plate containing the ECM extract made in step 2, at a density of $5\times10_4$ cells/cm$_2$. After incubation of 20-40 minutes allowing cells to attach, the cell-seeded extract is loaded onto the device to induce additional mechanical strain, and incubated at 37° C., 5% CO2. Culture is maintained for 7-10 days. Culture medium is changed every 3-4 days. Following 7-10 days the cell-seeded extract is transferred to a sterile hood and washed in PBS containing a protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation for three times. Verification of cell elimination is done using fluorescence microscopy and scanning electron microscopy imaging. Verification of modification of the extract is done using Western Blot, Enzyme-linked immunosorbent assay (ELISA), fluorescence microscopy and scanning electron microscopy imaging. Then the modified extract is solubilized and formulated into an injectable hydrophilic composition or to any other formulation, suitable for administration into a patient in need of that formulation, for the prevention and treatment of cancer.

Example 3

Preparation of Extracellular Extract Composition (III)

Cultured bone marrow-derived MSCs are harvested and grown on a device as described in Step 1 of Example 1. Then extracellular extract composition is prepared as described in Step 2 of Example 1.

Then the following modification step is applied:

Step 3: Modification of the Extracellular Extract

The ECM extract of Step 2 can be further modified by incubation with any desired type of cells to achieve a desired characteristic of the extract. One to more type of cells can be consecutively used for the modification step In order to modify the extract, cultured cells (such as for example, UC-MSCs or hESCs) are harvested using 0.25% trypsin-EDTA to detach the cells from the culture plates, which is subsequently neutralized with growth medium. Then cells are pelleted at approximately 200 g, resuspended in fresh growth medium, counted with a hemocytometer and seeded in the culture plate containing the ECM extract made in step 2, at a density of $5\times10_4$ cells/cm$_2$. After incubation of 20-40 minutes allowing cells to attach, the cell-seeded extract is loaded onto the device to induce additional mechanical strain, and incubated at 37° C., 5% CO2. Culture is maintained for 7-10 days. Culture medium is changed every 3-4 days. Verification of modification of the extract is done using Western Blot, Enzyme-linked immunosorbent assay (ELISA), fluorescence microscopy and scanning electron microscopy imaging.

In order to extract the entire range of intracellular and extracellular biomolecules of the modified extract, the following additional extraction method is applied:

Following the 7-10 days of culturing, the cell-seeded extract is transferred to a sterile hood and washed and homogenized in ice cold 3.4M NaCl buffer supplemented with a protease inhibitor cocktail (0.5 mM PMSF, 2 mM EDTA, 0.1M EACA, 2 mM NEM and the like). The homogenate is then centrifuged at 10,000 rpm at 4° C. for 15 minutes, following which the supernatant is discarded and pellets are resuspended in the 3.4M NaCl buffer. This step is repeated 2-3 times. Pellets are then resuspended in a 2M urea buffer, homogenized and stirred overnight at 4° C. Then the extract is centrifuged at 14,000 RPM at 4° C. for 30 minutes and the supernatant is reserved. Pellets are re-homogenized in half the original volume of 2M urea buffer then the centrifugation step is repeated. The supernatant is then combined with the previously reserved supernatant. Then the combined extract is dialyzed in 0.05 M Tris-saline buffer with chloroform (for sterilization) for two hrs in 4° C. then it is dialyzed in Tris-saline buffer several times, followed by DMEM. Then the extract is aliquoted into sterile tubes and stored in liquid nitrogen, or immediately used to be formulated to an injectable hydrophilic composition or to any other formulation, suitable for administration into a patient in need of that formulation, for the prevention and treatment of cancer.

Example 4

Preparation of Intracellular Extract Composition (I)

Materials and Methods

Preparation of Intracellular Extracts

Intracellular extracts are prepared as described for example in WO 02/057415.

For extract preparation the cell populations may be synchronized naturally or chemically. Cells may be arrested in any phase of the cell cycle, such as G0, interphase and mitosis, using standard procedures.

Cells may be incubated, for example, in low serum, such as 5%, 2%, or 0% serum, for 1, 2, 3, or more days to increase the percentage of cells in G0 phase. To synchronize cells in G1, the cells may be grown to confluence as attached cells and then incubated in 0.5-1 µg/ml nocodazole (Sigma Chemicals, St. Louis, Mo.) for 17-20 hours. The flasks containing the attached cells are shaken vigorously by repeatedly tapping the flasks with one hand, resulting in the detachment of mitotic cells and G1 phase doublets. The G1 phase doublets are pairs of elongated cells at the end of the division process that are still connected by a thin bridge. Detached G1 phase doublets may be isolated from the media based on this characteristic doublet structure. The G1 phase doublets may remain attached or may divide into two separate cells after isolation.

To increase the percentage of cells in S phase, the cells may be cultured in the presence of aphidicolin which inhibits DNA polymerase and thus inhibits DNA synthesis and arrests cells in S phase.

Alternatively, cells may be incubated in the presence of excess thymidine. The resulting high intracellular concentration of thymidine relative to that of other nucleotides also inhibits DNA polymerase.

Cells may be synchronized in G2 by incubating the cells in the presence of aphidicolin to arrest them in S phase and then washing the cells three times by repeated centrifugation and resuspension in phosphate buffered saline (PBS), as described herein. The cells are then incubated for a length of time sufficient for cells to enter G2 phase. For example, cells with a doubling time of approximately 24 hours, may be incubated for between 6 and 12 hours to allow them to enter G2 phase. For cells with shorter or longer doubling times, the incubation time may be adjusted accordingly.

Cells may be synchronized in mitosis by incubating them in 0.5 µg/ml nocodazole for 17-20 hours, and the mitotic cells are detached by vigorous shaking, as described above. The detached G1 phase doublets may be discarded, or they may be allowed to remain with the mitotic cells which constitute the majority (over 80%) of the detached cells. The harvested detached cells are centrifuged at 500 g for 10 minutes in a 10 ml conical tube at 4° C.

Synchronized or unsynchronized cells are harvested using standard methods and washed by centrifugation at 500 g for 10 minutes in a 10 ml conical tube at 4° C. The supernatant is discarded, and the cell pellet is resuspended in a total volume of 50 ml of cold PBS. The cells are centrifuged at 500 g for 10 minutes at 4° C. This washing step is repeated, and the cell pellet is resuspended in approximately 20 volumes of ice-cold interphase cell lysis buffer (20 mM Hepes, pH 8.2, 5 mM $MgCl_2$, 1 mM DTT, 10 pM aprotinin, 10 pM leupeptin, 10 pM pepstatin A, 10 pM soybean trypsin inhibitor, 100 pM PMSF, and optionally 20 pg/ml cytochalasin B). The cells are sedimented by centrifugation at 800 g for 10 minutes at 4° C. The supernatant is discarded, and the cell pellet is carefully resuspended in no more than one volume of interphase cell lysis buffer. The cells are incubated on ice for one hour to allow swelling of the cells. The cells are then lysed by either sonication using a tip sonicator or Dounce homogenization using a glass mortar and pestle. Cell lysis is performed until at least 90% of the cells and nuclei are lysed, which may be assessed using phase contrast microscopy. Duration and power of sonication required to lyse at least 90% of the cells and nuclei may vary depending on the type of cell used to prepare the extract.

The cell lysate is placed in a 1.5-ml centrifuge tube and centrifuged at 10,000 to 15,000 g for 15 minutes at 4° C. using a table top centrifuge.

The tubes are removed from the centrifuge and immediately placed on ice.

The supernatant is carefully collected using a 200 µl pipette tip, and the supernatant from several tubes is pooled and placed on ice. This supernatant is the cytoplasmic extract. This cell extract may be aliquoted into 20 pl volumes of extract per tube on ice and immediately flash-frozen on liquid nitrogen and stored at 80° C. until use.

Alternatively, the cell extract is placed in an ultracentrifuge tube on ice (e. g., fitted for an SW55 Ti rotor; Beckman). If necessary, the tube is overlayed with mineral oil to the top. The extract is centrifuged at 200,000 g for three hours at 4° C. to sediment membrane vesicles contained in the cytoplasmic extract. At the end of centrifugation, the oil is discarded. The supernatant is carefully collected, pooled if necessary, and placed in a cold 1.5 ml tube on ice. This supernatant is the cytosolic extract. The extract is aliquoted and frozen as described for the cytoplasmic extract.

Isolation of Cell Nuclei and Preparation of Nuclear Extracts

Cells are harvested in PBS using standard procedures, and several washing steps are performed to transfer the cells from their original media into a hypotonic buffer (10 mM Hepes, pH 7.5, 2 mM $MgCl_2$, 25 mM KCl, 1 mM DTT, 10 pM aprotinin, 10 pM leupeptin, 10 pM pepstatin A, 10 pM soybean trypsin inhibitor, and 100 pM PMSF). For example, the cells may be washed with 50 ml of PBS and pelleted by centrifugation at 500 g for 10 minutes at 4° C. The PBS supernatant is decanted, and the pelleted cells are resuspended in 50 ml of PBS and centrifuged, as described above. After this centrifugation, the pelleted cells are resuspended in 20-50 volumes of ice-cold hypotonic buffer and centrifuged at 500 g for 10 minutes at 4° C. The supernatant is again discarded and approximately 20 volumes of hypotonic buffer are added to the cell pellet. The cells are carefully resuspended in this buffer and incubated on ice for at least one hour, resulting in the gradual swelling of the cells.

To allow isolation of the nuclei from the cells, the cells are lysed using standard procedures. For example, 2-5 ml of the cell suspension may be transferred to a glass homogenizer and Dounce homogenized using an initial 10-20 strokes of a tight-fitting pestle. Alternatively, the cell suspension is homogenized using a motorized mixer (e. g., Ultraturrax). If desired, cell lysis may be monitored using phase contrast microscopy at 40-fold magnification. During this homogenization, the nuclei should remain intact and most or preferably all of the originally attached cytoplasmic components such as vesicles, organelles, and proteins should be released from the nuclei. If necessary, 1-20 µg/ml of the cytoskeletal inhibitors, cytochalasin B or cytochalasin D, may be added to the aforementioned hypotonic buffer to facilitate this process.

Homogenization is continued as long as necessary to lyse the cells and separate cytoplasmic components from the nuclei. For some cell types as many as 100, 150, or more strokes may be required. The lysate is then transferred into a 15 ml conical tube on ice, and the cell lysis procedure is repeated with the remainder of the suspension of swollen cells. Sucrose from a 2M stock solution made in hypotonic buffer is added to the cell lysate, resulting in a final concentration of 250 mM sucrose. This solution is mixed by inversion, and the nuclei are pelleted by centrifugation at 400 g in a swing out rotor for 10 to 40 minutes at 4° C. The supernatant is then discarded, and the pelleted nuclei are resuspended in 10-20 volumes of nuclear buffer (10 mM Hepes, pH 7.5, 2 mM $MgCl_2$, 250 mM sucrose, 25 mM KCl, 1 mM DTT, 10 pM aprotinin, 10 pM leupeptin, 10 pM pepstatin A, 10 pM soybean trypsin inhibitor, and 100 pM PMSF). The nuclei are sedimented and resuspended in 1-2 volumes of nuclear buffer, as described above. The freshly isolated nuclei may either be used immediately for extract preparation or stored for future use. For storage, the nuclei are diluted in nuclear buffer to a concentration of approximately $10^6$/ml. Glycerol (2.4 volumes of 100% glycerol) is added and mixed well by gentle pipetting. The suspension is aliquoted into 100-500 all volumes in 1.5-ml tubes on ice, immediately frozen in a methanol-dry ice bath, and stored at −80° C. Prior to use, aliquots of the nuclei are thawed on ice or at room temperature. One volume of ice-cold nuclear buffer is added, and the solution is centrifuged at 1,000 g for 15 minutes in a swing out rotor. The pelleted nuclei are resuspended in 100-500 µl nuclear-buffer and centrifuged as described above. The pelleted nuclei are then resuspended in a minimal volume of nuclear buffer and stored on ice until use.

Preparation of Nuclear Extract

The nuclei are lysed by either sonication using a tip sonicator or Dounce homogenization using a glass mortar and pestle. Duration and power of sonication required may vary depending on the type of cell used to prepare the extract. The nuclear extract is derived by a 10-60 minute incubation in nuclear buffer containing NaCl or KCl at a concentration of 0.15-800 mM under agitation. The lysate is centrifuged to sediment unextractable components. The supernatant containing the extract is dialyzed to eliminate the NaCl or KCl. The dialyzed nuclear extract is aliquoted and stored frozen.

Preparation of Whole Cell Extracts

The cultured cells are rinsed 3-4 times with PBS, and culture medium, such as alpha-MEM or DMEM/F12 (Gibco) is added without additives or serum. 12-24 hours later, the cells are washed twice with PBS and harvested, preferably scraped with a rubber policeman and collected in a 50 ml Falcon tube (Becton Dickinson). Then cells are washed and resuspended in ice-cold cell lysis buffer (20 mM HEPES, pH 8.2, 50 mM NaCl, 5 mM $MgCl_2$, 1 mM dithiothreitol and a protease inhibitor cocktail), sedimented at 400 g and resuspended in one volume of cell lysis buffer. Cells are sonicated on ice in 200 µl aliquots using a sonicator fitted with a 2-mm diameter probe until all cells and nuclei are lysed, as can be judged by phase contrast microscopy. The lysate is centrifuged at 10,000-14,000 g, 15-30 minutes at 4° C. to pellet the coarse material and any potentially remaining non-lysed cell. The supernatant is aliquoted, frozen and stored in liquid nitrogen or immediately used. Protein concentration of the extract is analyzed by Bradford assay, pH is adjusted to around 7.0±0.4 and oslolarity is adjusted to −300 mOsm prior to use, in necessary, (by diluting with water).

Combination of Whole Cell Extract with Nuclear Extract

If desired, whole cell extract can be enriched with additional nuclear factors. Nuclei are purified for example from cells of the cell type from which the extract is derived and nuclear extract is prepared as described above. The nuclear extract is added at various concentrations to the whole cell extract described above.

Step 1: Seeding of Cells

In order to facilitate extracellular matrix formation and induce alignment of cells and provide mechanical cues, cells can be seeded and grown on the device as described in Step 1 of Example 1. Alternatively, cells can be grown on standard tissue culture plates or by any other method known in the art.

Cultured bone marrow-derived MSCs are harvested using 0.25% trypsin-EDTA to detach the cells from the culture plates, which is subsequently neutralised with growth medium. Then cells are pelleted at approximately 500 g, resuspended in fresh growth medium, counted with a hemocytometer seeded onto the silicone substrate of the culture device at a density of $2 \times 10^3$ cells/$cm^2$. After incubation of 30-40 minutes allowing cells to attach, a pre-defined training program is initiated to apply a uniform cyclic strain of 2-4%, at a 0.2 Hz frequency. When the culture reaches approximately 50-60% confluency, the training program is stopped and cells are harvested in their exponential growth phase to benefit from maximal transcriptional activity. Tissue formation is verified by histological analysis, and by using scanning electron microscopy imaging.

Step 2: Preparation of Intracellular Extract Composition

MSCs described in Step 1 are harvested from the culture device in their exponential growth phase when the culture reaches approximately 50-60% confluency. Then the cells are synchronized in the desired cell cycle phase, such as in G1 phase, according to the method described above. Then the synchronized cells are harvested, and an intracellular compartment is extracted using the method described above. Then the extract is aliquoted into sterile tubes and stored in liquid nitrogen, or solubilized and formulated into an injectable hydrophilic composition, or to any other formulation, suitable for administration into a patient in need of that formulation, for the prevention and treatment of cancer.

Example 5

Preparation of Intracellular Extract Composition (II)

Step 1: Preparation of Intracellular Extract from Human Bone Marrow-Derived MSCs Human non marrow-derived MSCs are cultured according to methods described in Example 4 above, harvested in their exponential growth phase before their intracellular compartment is extracted according to the same methods described in Example 4 above.

Step 2: Preparation of a Scaffold from the Intracellular Extract

Scaffolds can be fabricated from extracts by any suitable method known in the art, for example as described in WO009/098698.

In the following step, a scaffold is fabricated by Electro-Spinning:

The intracellular extract generated in step 1 is lyophilized in a lyophilizer for 2 days. Then the lyophilized extract is dissolved in 1,1,1,3,3,3 Hexafluoro-2-Propanol (HFP) (Sigma). The Extract solution is left to stir at least 24 hours at room temperature, or in ~50° C. water-bath for overnight before electro-spinning, to ensure complete dissolution. The supernatant is collected for electrospinning.

Fibers are electrospun by using a syringe pump (Fisher) to eject solution from a 3 ml syringe through an 18-gauge needle at a delivery rate of 0.5-1.0 ml/h, an air gap distance of 10-15 cm, and accelerating voltage of 12-20 kV. Fibers are collected onto an aluminum collector. For measurement of fiber diameters, glass coverslips coated with electrospun fibers are mounted onto metal stubs with carbon tape and sputter-coated for 30 sec with platinum and palladium prior to visualization in an environmental scanning electron microscope.

Step 3: Modification of the Electrospun Intracellular Extract-Derived Scaffold

The electrospun scaffold of Step 2 can be further modified by incubation with any desired type of cells to achieve a desired characteristic of the scaffold. One to more type of cells can be consecutively used for the modification step.

In order to modify the scaffold, cultured cells (such as for example, UC-MSCs or hESCs) are harvested using 0.25% trypsin-EDTA to detach the cells from the culture plates, which is subsequently neutralized with growth medium. Then cells are pelleted at approximately 200 g, resuspended in fresh growth medium, counted with a hemocytometer and seeded on the scaffold made in step 2, at a density of $5 \times 10_4$ cells/cm$_2$. After incubation of 20-40 minutes allowing cells to attach, the cell-seeded scaffold is loaded onto the device to induce additional mechanical strain, and incubated at 37° C., 5% CO2. Culture is maintained for 7-10 days. Culture medium is changed every 3-4 days. Following 7-10 days the cell-seeded scaffold is transferred to a sterile hood and washed in PBS containing a protease inhibitor cocktail (Sigma) for 30 minutes with agitation, then incubated with agitation in 0.3% sodium dodecyl sulphate (SDS) in a Tris buffer for 12-24 hours at room temperature, then washed in PBS for 10 minutes with agitation for three times. Verification of cell elimination is done using fluorescence microscopy and scanning electron microscopy imaging. Verification of modification of the scaffold is done using Western Blot, Enzyme-linked immunosorbent assay (ELISA), fluorescence microscopy and scanning electron microscopy imaging. Then the modified scaffold is solubilized and formulated into an injectable hydrophilic composition or to any other formulation, suitable for administration into a patient in need of that formulation, for the prevention and treatment of cancer.

REFERENCES

1. Szyf, M. Therapeutic implications of DNA methylation. *Future Oncol* 1, 125-135 (2005).
2. Collas, P. & Gammelsaeter, R. Novel approaches to epigenetic reprogramming of somatic cells. *Cloning Stem Cells* 9, 26-32 (2007).
3. Hendrix, M. J. et al. Reprogramming metastatic tumour cells with embryonic microenvironments. *Nat Rev Cancer* 7, 246-255 (2007).
4. Ingber D. E. Can cancer be reversed by engineering the tumor microenvironment? *Semin Cancer Biol.* 18(5):356-64 (2008).

The invention claimed is:

1. A pharmaceutical composition, consisting essentially of therapeutically effective amounts of a stem cell extract, collagen, elastin, hyaluronic acid, fibronectin and laminin.

2. The pharmaceutical composition according to claim 1, wherein said stem cell extract is a mammalian stem cell extract.

3. The pharmaceutical composition according to claim 1, wherein said stem cell extract is a human stem cell extract.

4. The pharmaceutical composition according to claim 1, wherein the stem cell extract is prepared from a cell or a tissue selected from the group consisting of a primary stem cell, a cultured stem cell, a stem cell line, an engineered stem cell tissue, and a primary stem cell tissue.

5. The pharmaceutical composition according to claim 4, wherein said stem cell extract is a cell extract selected from the group consisting of embryonic stem cell extract, undifferentiated stem cell extract, pluripotent stem cell extract, lineage-restricted stem cell extract, precursor stem cell extract, somatic stem cell extract, terminally differentiated somatic stem cell extract, extract of stem cells expressing one or more markers of multilineage differentiation potential, extract of stem cells expressing one or more markers of pluripotent stem cells, hematopoietic stem cell extract, neural stem cell extract, mesenchymal stem cell extract, and fetal stem cell extract.

6. The pharmaceutical composition according to claim 1, wherein the stem cell extract is selected from the group consisting of a cytosolic stem cell extract, a cytoplasmic stem cell extract, a nuclear stem cell extract, a whole stem cell lysate, an extracellular stem cell extract, a whole tissue stem cell extract, and mixtures thereof.

7. The pharmaceutical composition according to claim 1, wherein the stem cell extract is prepared from a stem cell or a stem cell tissue which is cultured in a cell culture device capable of exerting mechanical forces onto the cultured stem cells or stem cell tissue and has a patterned surface.

8. A method for preparing the pharmaceutical composition of claim 1, consisting essentially of:

a. obtaining stem cells or stem cell tissues;
b. preparing extracellular extracts and/or intracellular extracts from said stem cells or stem cell tissues; and
c. formulating the extracellular extracts and/or intracellular extracts from said stem cells or stem cell tissues to obtain the composition of claim 1 consisting essentially of a stem cell extract, collagen, elastin, hyaluronic acid, fibronectin and laminin.

9. A method for preparing the pharmaceutical composition of claim 1, consisting essentially of:
i. obtaining stem cells or stem cell tissues:
ii. preparing extracellular extracts and/or intracellular extracts from said stem cells or stem cell tissues;
iii. seeding at least one type of cells on said stem cell or stem cell tissue extract;
iv. eliminating the cells from the stem cell or stem cell tissue extract; and
v. formulating the extracellular extracts and/or intracellular extracts from said stem cells or stem cell tissues to obtain the composition of claim 1 consisting essentially of a stem cell extract, collagen, elastin, hyaluronic acid, fibronectin and laminin.

10. A method for preparing the pharmaceutical composition of claim 1, consisting essentially of:
i. obtaining stem cells or stem cell tissues:
ii. preparing extracellular extracts and/or intracellular extracts from said stem cells or stem cell tissues;
iii. preparing a scaffold from said stem cell or stem cell tissue extract;
iv. seeding at least one type of cells on the scaffold;
iv. eliminating the cells from the scaffold; and
v. formulating the scaffold to obtain the composition of claim 1 consisting essentially of a stem cell extract, collagen, elastin, hyaluronic acid, fibronectin and laminin.

11. The method according to claim 8, wherein said intracellular stem cell extracts are prepared from separate cellular compartments, selected from the group consisting of a cytosolic compartment, a cytoplasmic compartment, a nuclear compartment, and any combination thereof.

12. The method according to claim 8, wherein, prior to step (b), said stem cells or stem cell tissues are cultured in a cell culture device capable of exerting mechanical forces onto the cultured stem cells or stem cell tissues and has a patterned surface.

13. The method according to claim 9, wherein steps (iii) and (iv) are repeated at least twice.

14. The method according to claim 10, wherein steps (iv) and (v) are repeated at least twice.

* * * * *

UNITED STATES PATENT AND TRADEMARK OFFICE
CERTIFICATE OF CORRECTION

PATENT NO. : 8,778,416 B2
APPLICATION NO. : 13/578402
DATED : July 15, 2014
INVENTOR(S) : Shahar Cohen It is certified that error appears in the above-identified patent and that said Letters Patent is hereby corrected as shown below:

Claims:

At column 46, claim 10, line 7, change "iv" to read --v--.
At column 46, claim 10, line 8, change "v" to read --vi--.

Signed and Sealed this
Second Day of August, 2016

Michelle K. Lee
*Director of the United States Patent and Trademark Office*